(12) United States Patent
Wilson et al.

(10) Patent No.: US 9,365,516 B2
(45) Date of Patent: Jun. 14, 2016

(54) PROCESS FOR PREPARING QUINOLINE DERIVATIVES

(71) Applicant: Exelixis, Inc., South San Francisco, CA (US)

(72) Inventors: Jo Ann Wilson, San Francisco, CA (US); Sriram Naganathan, San Jose, CA (US); Neil G. Andersen, Montara, CA (US); Matthew Pfeiffer, Salt Lake City, UT (US)

(73) Assignee: Exelixis, Inc., South San Francisco, CA (US)

( * ) Notice: Subject to any disclaimer, the term of this patent is extended or adjusted under 35 U.S.C. 154(b) by 0 days.

(21) Appl. No.: 14/353,251

(22) PCT Filed: Oct. 22, 2012

(86) PCT No.: PCT/US2012/061320
§ 371 (c)(1),
(2) Date: Apr. 21, 2014

(87) PCT Pub. No.: WO2013/059788
PCT Pub. Date: Apr. 25, 2013

(65) Prior Publication Data
US 2014/0256938 A1  Sep. 11, 2014

Related U.S. Application Data

(60) Provisional application No. 61/549,312, filed on Oct. 20, 2011.

(51) Int. Cl.
| | | |
|---|---|---|
| *C07D 239/72* | (2006.01) | |
| *C07D 215/00* | (2006.01) | |
| *C07D 215/233* | (2006.01) | |
| *C07D 239/90* | (2006.01) | |
| *C07C 231/02* | (2006.01) | |

(52) U.S. Cl.
CPC .......... *C07D 215/233* (2013.01); *C07C 231/02* (2013.01); *C07D 215/00* (2013.01); *C07D 239/90* (2013.01)

(58) Field of Classification Search
USPC .......................................... 544/128; 546/153
See application file for complete search history.

(56) References Cited

U.S. PATENT DOCUMENTS

2010/0081805 A1   4/2010   Deschamps et al.

FOREIGN PATENT DOCUMENTS

| WO | 2009136663 A1 | 11/2009 |
| WO | 2010056960 A1 | 5/2010 |
| WO | 2010083414 A1 | 7/2010 |

OTHER PUBLICATIONS

Saavedra, et al., "N<3>-Arylmalonamides: A new series of thieno[3,2-b]pyridine based inhibitors of c-Met and VEGFR2 tyrosine kinases." Bioorganic & Medicinal Chemistry Letters, 19(24): 6836-6839, 2009.
International Search Report for PCT/US2012/061320 mailed Jan. 25, 2013.

*Primary Examiner* — Jeffrey H Murray
(74) *Attorney, Agent, or Firm* — Honigman Miller Schwartz and Cohn, LLP; Heidi M. Berven; Jonathan P. O'Brien

(57) ABSTRACT

A process for preparing a compound of Formula I is disclosed:

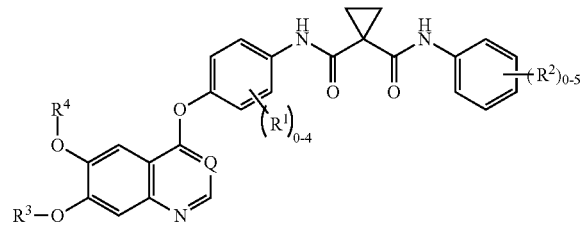

wherein:
$R^1$ is halo;
$R^2$ is halo;
$R^3$ is $(C_1-C_6)$alkyl or $(C_1-C_6)$alkyl optionally substituted with heterocycloalkyl;
$R^4$ is $(C_1-C_6)$alkyl; and
Q is CH or N;

comprising:
(a) contacting 1,1-cyclopropane dicarboxylic acid with thionyl chloride in a polar aprotic solvent;
(b) adding

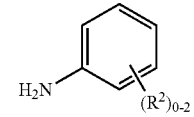

and a tertiary amine base to the mixture of step (a) to form a compound of Formula A; and

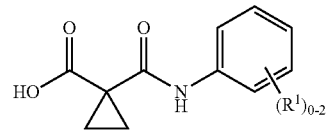

(c) coupling a compound of Formula A with an amine of Formula B to form a compound of Formula I.
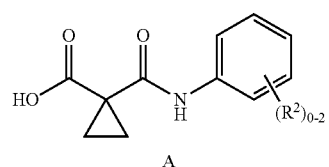
A
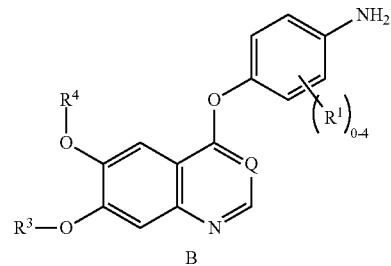
B
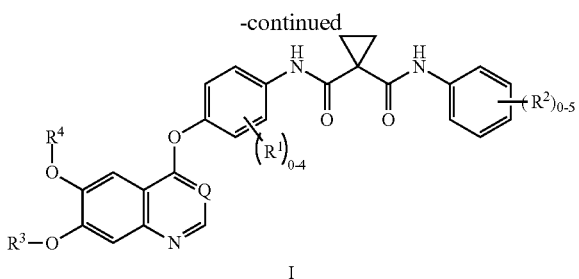
I
28 Claims, No Drawings

PROCESS FOR PREPARING QUINOLINE DERIVATIVES

CROSS-REFERENCE TO RELATED APPLICATIONS

This application is a United States National Phase filing of PCT/US2012/061320, filed Oct. 22, 2012, which claims the benefit of priority of U.S. Provisional Application No. 61/549,312, filed Oct. 20, 2011, all of which are incorporated herein by reference.

FIELD OF THE INVENTION

This disclosure relates to process of preparing compounds useful for modulating protein kinase enzymatic activity. More specifically, this disclosure relates to a process for preparing compounds useful for modulating cellular activities such as proliferation, differentiation, programmed cell death, migration, and chemoinvasion.

BACKGROUND OF THE INVENTION

Modulation (particularly inhibition) of cell proliferation and angiogenesis, two key cellular processes needed for tumor growth and survival (Matter A. Drug Disc Technol 20016, 1005-1024) is an attractive goal for development of small-molecule drugs. Anti-angiogenic therapy represents a potentially important approach for the treatment of solid tumors and other diseases associated with dysregulated vascularization, including ischemic coronary artery disease, diabetic retinopathy, psoriasis, and rheumatoid arthritis. As well, cell antiproliferative agents are desirable to slow or stop the growth of tumors.

One such target for small-molecule modulation of antiangiogenic and antiproliferative activity is c-Met. The kinase c-Met, is the prototypic member of a subfamily of heterodimeric receptor tyrosine kinases (RTKs) which include Met, Ron and Sea. Expression of c-Met occurs in a wide variety of cell types including epithelial, endothelial, and mesenchymal cells where activation of the receptor induces cell migration, invasion, proliferation and other biological activities associated with "invasive cell growth." As such, signal transduction through c-Met receptor activation is responsible for many of the characteristics of tumor cells.

N-(4-{[6,7-bis(methyloxy)quinolin-4-yl]oxy}phenyl)-N'-(4-fluorophenyl)cyclopropane-1,1-dicarboxamide and N-[3-fluoro-4-({6-(methyloxy)-7-[(3-morpholin-4-ylpropyl)oxy]quinolin-4-yl}oxy)phenyl]-N'-(4-fluorophenyl)cyclopropane-1,1-dicarboxamide are two small molecule inhibitors of c-Met that are currently undergoing clinical investigation as treatments for a range of cancers. There is accordingly an ongoing need for new and efficient processes for making these two promising cancer therapies.

SUMMARY OF THE INVENTION

These and other needs are met by the present invention which is directed to a process for preparing a compound of Formula A:

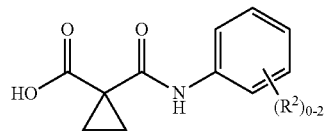

wherein $R^2$ is H, F, Cl, or Br;

comprising (a) contacting 1,1-cyclopropane dicarboxylic acid with thionyl chloride in a polar aprotic solvent; and (b) adding

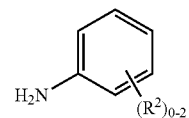

and a tertiary amine base to the mixture of step (a).

The compound of Formula A is used to form a compound of Formula I:

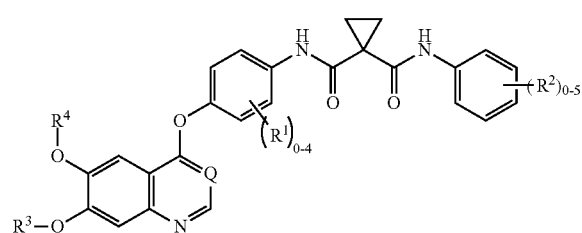

wherein:

$R^1$ is halo;

$R^2$ is halo;

$R^3$ is $(C_1-C_6)$alkyl or $(C_1-C_6)$alkyl optionally substituted with heterocycloalkyl;

$R^4$ is $(C_1-C_6)$alkyl; and

Q is CH or N.

In one embodiment, the compound of Formula I is compound 1:

Compound 1

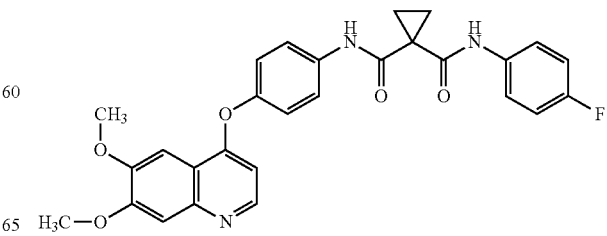

or a pharmaceutically acceptable salt thereof. Compound 1 is known as N-(4-{[6,7-bis(methyloxy)quinolin-4-yl]oxy}phenyl)-N'-(4-fluorophenyl)cyclopropane-1,1-dicarboxamide. WO 2005/030140 describes the synthesis of N-(4-{[6,7-bis(methyloxy)quinolin-4-yl]oxy}phenyl)-N'-(4-fluorophenyl)cyclopropane-1,1-dicarboxamide (Example 12, 37, 38, and 48) and also discloses the therapeutic activity of this molecule to inhibit, regulate, and/or modulate the signal transduction of kinases, (Assays, Table 4, entry 289). Example 48 is on paragraph [0353] in WO 2005/030140, the entire contents of which is incorporated by reference.

In another embodiment, the compound of Formula I is compound 2:

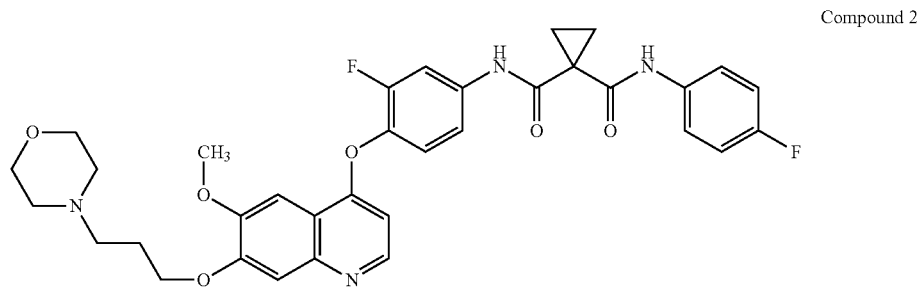 [SMILES: COc1cc2c(Oc3ccc(NC(=O)C4(C(=O)Nc5ccc(F)cc5)CC4)cc3F)ccnc2cc1OCCCN1CCOCC1]

or a pharmaceutically acceptable salt thereof. Compound 2 is known as is N-[3-fluoro-4-({6-(methyloxy)-7-[(3-morpholin-4-ylpropyl)oxy]quinolin-4-yl}oxy)phenyl]-N'-(4-fluorophenyl)cyclopropane-1,1-dicarboxamide. WO 2005-030140 describes the synthesis of Compound (I) (Examples 25, 30, 36, 42, 43 and 44) and also discloses the therapeutic activity of this molecule to inhibit, regulate, and/or modulate the signal transduction of kinases, (Assays, Table 4, entry 312). Compound 2 has been measured to have a c-Met $IC_{50}$ value of approximately 0.6 nanomolar (nM). PCT/US09/064341, which claims priority to U.S. provisional application 61/199,088, filed Nov. 13, 2008, describes a scaled-up synthesis of compound 2.

Thus in another aspect, the invention is directed to a process for preparing a compound of Formula I as defined above;

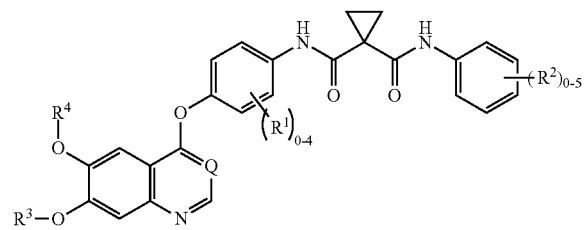

comprising the steps of (a) contacting 1,1-cyclopropane dicarboxylic acid with thionyl chloride in a polar aprotic solvent;

(b) adding

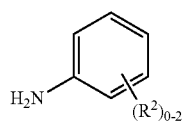

and a tertiary amine base to the mixture of step (a) to form a compound of Formula A; and

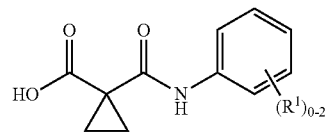

(c) coupling a compound of Formula A with an amine of Formula B to form a compound of Formula I

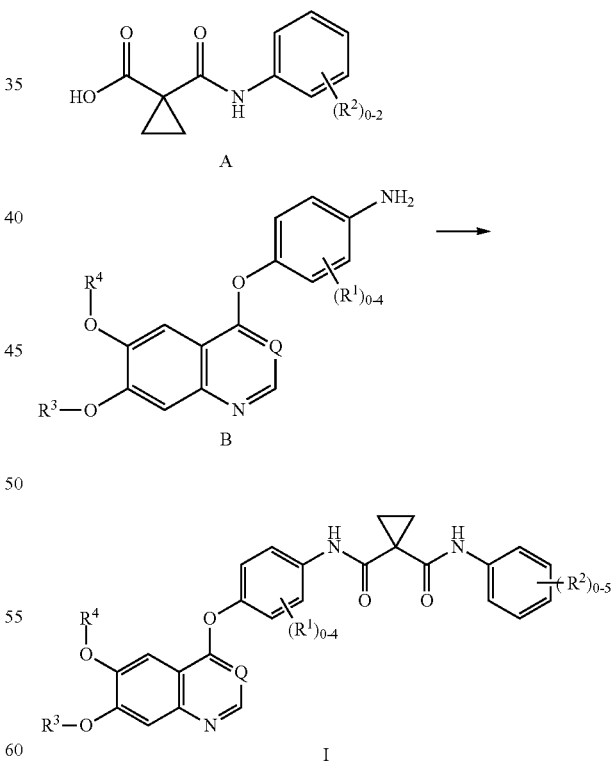

The Compound of Formula B can be prepared as described in WO 2005/030140, as mentioned previously, the entire contents of which is incorporated by reference. Alternative approaches to the synthesis of the compound of Formula I, compound A, compound B, and Compounds 1 and 2 are disclosed in additional applications PCT/2009/643411 and PCT/US2010/021194, and the entire contents of each are disclosed herein by reference.

The mono-amidation process disclosed and claimed herein presents several significant processing advantages. Prior approaches to making Compound A required mixing 1,1-cyclopropanedicarboxylic acid with triethyl amine, and then adding thionyl chloride followed by the aniline. The reaction was typically and undesirably exothermic. The inventors found that the exotherm was eliminated by reordering the sequence of reagent additions. Reaction times were significantly reduced, and the resulting product does not require additional purification. Moreover, the invention process as disclosed herein is highly selective for formation of the mono-amidation product Compound A.

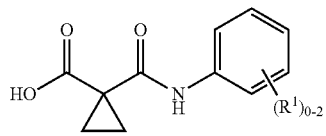

over the bis-amide

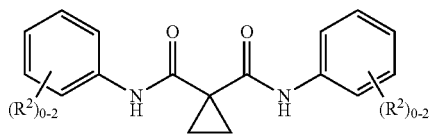

A

The bis-amide, if present, is readily removed using the isolation conditions developed by the inventors.

The process as claimed herein is generalizable for the selective mono-amidation of symmetric dicarboxylic acids using an array of primary or secondary amines. Thus, in another aspect, the invention provides a process for making a mono-amide from the corresponding dicarboxylic acid, comprising:

(a) contacting a dicarboxylic acid with thionyl chloride in a polar aprotic solvent; and (b) adding a primary amine and a tertiary amine base to the resulting mixture.

There are many different aspects and embodiments of the disclosure described herein below, and each aspect and each embodiment is non-limiting in regard to the scope of the disclosure. The terms "aspects" and "embodiments" are meant to be non-limiting regardless of where the terms "aspect" or "embodiment" appears in this specification. The transitional term "comprising" as used herein, which is synonymous with "including," "containing," or "characterized by," is inclusive or open-ended and does not exclude additional, unrecited elements.

DETAILED DESCRIPTION OF THE INVENTION

Abbreviations and Definitions

The following abbreviations and terms have the indicated meanings throughout:

| Abbreviation | Meaning |
| --- | --- |
| Ac | Acetyl |
| br | Broad |
| ° C. | Degrees Celsius |
| c— | Cyclo |
| CBZ | CarboBenZoxy=benzyloxycarbonyl |
| d | Doublet |
| dd | Doublet of doublet |
| dt | Doublet of triplet |
| DCM | Dichloromethane |
| DMA | N,N-dimethylacetamide |
| DME | 1,2-dimethoxyethane |
| DMF | N,N-Dimethylformamide |
| DMSO | dimethyl sulfoxide |
| Dppf | 1,1'-bis(diphenylphosphano)ferrocene |
| DSC | Differential scanning calorimetry |
| EI | Electron Impact ionization |
| Et | Ethyl |
| g | Gram(s) |
| GVS | Gravimetric vapor sorption |
| h or hr | Hour(s) |
| HPLC | High pressure liquid chromatography |
| KF | Karl Fisher water content determination |
| kg | Kilogram |
| kV | Kilovolt |
| L | Liter(s) |
| LCMS | Liquid chromatography-Mass spectrometry |
| mA | Milliampere |
| Me | Methyl |
| M | Molar or molarity |
| m | Multiplet |
| Mm | Millimeter |
| MEK | Methyl ethyl ketone |
| mg | Milligram(s) |
| MHz | Megahertz (frequency) |
| Min | Minute(s) |
| mL | Milliliter(s) |
| µL | Microliter(s) |
| µm | Micrometer |
| µM | Micromole(s) or micromolar |
| mM | Millimolar |
| mmol | Millimole(s) |
| Mol | Mole(s) |
| MS | Mass spectral analysis |
| MTBE | Methyl t-butyl ether |
| N | Normal or normality |
| nM | Nanomolar |
| NMR | Nuclear magnetic resonance spectroscopy |
| q | Quartet |
| psi | Pounds per square inch |
| rpm | Revolutions per minute |
| RH | Relative humidity |
| RT | Room temperature |
| s | Singlet |
| t or tr | Triplet |
| TFA | Trifluoroacetic acid |
| TGA | Thermogravimetric analysis |
| THF | Tetrahydrofuran |
| TLC | Thin layer chromatography |
| XRPD | X-ray powder diffraction |
| θ | Angle rotation in radians |

The symbol "—" means a single bond; "=" means a double bond.

When chemical structures are depicted or described, unless explicitly stated otherwise, all carbons are assumed to have hydrogen substitution to conform to a valence of four. For example, in the structure on the left-hand side of the schematic below there are nine hydrogens implied. The nine hydrogens are depicted in the right-hand structure. Sometimes a particular atom in a structure is described in textual formula as having a hydrogen or hydrogens as substitution (expressly defined hydrogen), for example, —CH$_2$CH$_2$—. It is understood by one of ordinary skill in the art that the aforementioned descriptive techniques are common in the chemical arts to provide brevity and simplicity to description of otherwise complex structures.

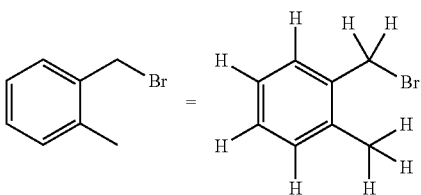

If a group "R" is depicted as "floating" on a ring system, as for example in the formula:

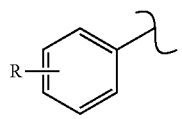

then, unless otherwise defined, a substituent "R" may reside on any atom of the ring system, assuming replacement of a depicted, implied, or expressly defined hydrogen from one of the ring atoms, so long as a stable structure is formed.

If a group "R" is depicted as floating on a fused ring system, as for example in the formulae:

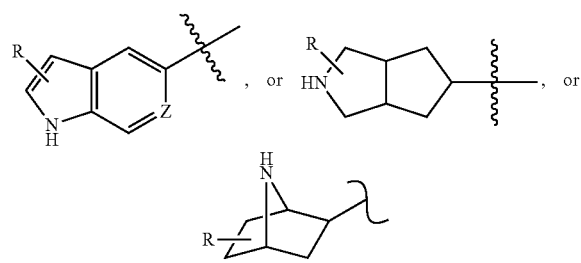

then, unless otherwise defined, a substituent "R" may reside on any atom of the fused ring system, assuming replacement of a depicted hydrogen (for example the —NH— in the formula above), implied hydrogen (for example as in the formula above, where the hydrogens are not shown but understood to be present), or expressly defined hydrogen (for example where in the formula above, "Z" equals =CH—) from one of the ring atoms, so long as a stable structure is formed. In the example depicted, the "R" group may reside on either the 5-membered or the 6-membered ring of the fused ring system. When a group "R" is depicted as existing on a ring system containing saturated carbons, as for example in the formula:

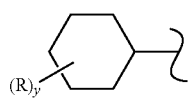

where, in this example, "y" can be more than one, assuming each replaces a currently depicted, implied, or expressly defined hydrogen on the ring; then, unless otherwise defined, where the resulting structure is stable, two "R's" may reside on the same carbon. A simple example is when R is a methyl group; there can exist a geminal dimethyl on a carbon of the depicted ring (an "annular" carbon). In another example, two R's on the same carbon, including that carbon, may form a ring, thus creating a spirocyclic ring (a "spirocyclyl" group) structure with the depicted ring as for example in the formula.

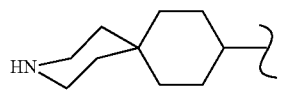

"$(C_1-C_6)$Alkyl" or "alkyl" means a linear or branched hydrocarbon group having one to six carbon atoms. Examples of lower alkyl groups include methyl, ethyl, propyl, isopropyl, butyl, s-butyl, t-butyl, isobutyl, pentyl, hexyl, and the like. "$C_6$ alkyl" refers to, for example, n-hexyl, iso-hexyl, and the like.

"Heterocycloalkyl" means a saturated or partially unsaturated monovalent monocyclic group of 3 to 8 ring atoms or a saturated or partially unsaturated monovalent fused bicyclic group of 5 to 12 ring atoms in which one or more, for example one, two, three, or four ring heteroatoms independently selected from —O—, —$S(O)_n$— (n is 0, 1, or 2), —N=, —N($R^y$)— (where $R^y$ is hydrogen, alkyl, hydroxy, alkoxy, acyl, or alkylsulfonyl), the remaining ring atoms being carbon. One or two ring carbon atoms may be replaced by a —C(O)—, —C(S)—, or —C(=NH)— group. Fused bicyclic radical includes bridged ring systems. Unless otherwise stated, the valency of the group may be located on any atom of any ring within the radical, valency rules permitting. In particular, when the point of valency is located on a nitrogen atom, $R^y$ is absent. In another embodiment the term heterocycloalkyl includes, but is not limited to, azetidinyl, pyrrolidinyl, 2-oxopyrrolidinyl, 2,5-dihydro-1H-pyrrolyl, piperidinyl, 4-piperidonyl, morpholinyl, piperazinyl, 2-oxopiperazinyl, tetrahydropyranyl, 2-oxopiperidinyl, thiomorpholinyl, thiamorpholinyl, perhydroazepinyl, pyrazolidinyl, imidazolinyl, imidazolidinyl, dihydropyridinyl, tetrahydropyridinyl, oxazolinyl, oxazolidinyl, isoxazolidinyl, thiazolinyl, thiazolidinyl, quinuclidinyl, isothiazolidinyl, octahydroindolyl, octahydroisoindolyl, decahydroisoquinolyl, tetrahydrofuryl, and tetrahydropyranyl, and the derivatives thereof, and N-oxide or a protected derivative thereof.

"Halogen" or "halo" refers to fluorine, chlorine, bromine or iodine.

"Yield" for each of the reactions described herein is expressed as a percentage of the theoretical yield.

"Patient" for the purposes of the present invention includes humans and other animals, particularly mammals, and other organisms. Thus the processes are applicable to both human therapy and veterinary applications. In another embodiment the patient is a mammal, and in another embodiment the patient is human.

A "pharmaceutically acceptable salt" of a compound means a salt that is pharmaceutically acceptable and that possesses the desired pharmacological activity of the parent compound. It is understood that the pharmaceutically acceptable salts are non-toxic. Additional information on suitable pharmaceutically acceptable salts can be found in *Remington's Pharmaceutical Sciences*, 17th ed., Mack Publishing Company, Easton, Pa., 1985, which is incorporated herein by reference or S. M. Berge, et al., "Pharmaceutical Salts," J. Pharm. Sci., 1977; 66:1-19, both of which are incorporated herein by reference.

Examples of pharmaceutically acceptable acid addition salts include those formed with inorganic acids such as hydrochloric acid, hydrobromic acid, sulfuric acid, nitric acid, phosphoric acid, and the like; as well as organic acids such as acetic acid, trifluoroacetic acid, propionic acid, hexanoic acid, cyclopentanepropionic acid, glycolic acid, pyruvic acid, lactic acid, oxalic acid, maleic acid, malonic acid, succinic acid, fumaric acid, tartaric acid, malic acid, citric acid, benzoic acid, cinnamic acid, 3-(4-hydroxybenzoyl)benzoic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, p-toluenesulfonic acid, and salicylic acid and the like.

"Prodrug" refers to compounds that are transformed (typically rapidly) in vivo to yield the parent compound of the above formulae, for example, by hydrolysis in blood. Common examples include, but are not limited to, ester and amide forms of a compound having an active form bearing a carboxylic acid moiety. Examples of pharmaceutically acceptable esters of the compounds of this invention include, but are not limited to, alkyl esters (for example with between approximately one and approximately six carbons) the alkyl group is a straight or branched chain. Acceptable esters also include cycloalkyl esters and arylalkyl esters such as, but not limited to benzyl. Examples of pharmaceutically acceptable amides of the compounds of this invention include, but are not limited to, primary amides, and secondary and tertiary alkyl amides (for example with between approximately one and approximately six carbons). Amides and esters of the compounds of the present invention may be prepared according to conventional processes. A thorough discussion of prodrugs is provided in T. Higuchi and V. Stella, "Pro-drugs as Novel Delivery Systems," Vol 14 of the A.C.S. Symposium Series, and in Bioreversible Carriers in Drug Design, ed. Edward B. Roche, American Pharmaceutical Association and Pergamon Press, 1987, both of which are incorporated herein by reference for all purposes.

"Therapeutically effective amount" is an amount of a compound of the invention, that when administered to a patient, ameliorates a symptom of the disease. A therapeutically effective amount is intended to include an amount of a compound alone or in combination with other active ingredients effective to modulate c-Met, and/or VEGFR2, or effective to treat or prevent cancer. The amount of a compound of the invention which constitutes a "therapeutically effective amount" will vary depending on the compound, the disease state and its severity, the age of the patient to be treated, and the like. The therapeutically effective amount can be determined by one of ordinary skill in the art having regard to their knowledge and to this disclosure.

"Treating" or "treatment" of a disease, disorder, or syndrome, as used herein, includes (i) preventing the disease, disorder, or syndrome from occurring in a human, i.e. causing the clinical symptoms of the disease, disorder, or syndrome not to develop in an animal that may be exposed to or predisposed to the disease, disorder, or syndrome but does not yet experience or display symptoms of the disease, disorder, or syndrome; (ii) inhibiting the disease, disorder, or syndrome, i.e., arresting its development; and (iii) relieving the disease, disorder, or syndrome, i.e., causing regression of the disease, disorder, or syndrome. As is known in the art, adjustments for systemic versus localized delivery, age, body weight, general health, sex, diet, time of administration, drug interaction and the severity of the condition may be necessary, and will be ascertainable with routine experience.

Process

In one aspect, this disclosure relates to a process for preparing a compound of Formula A:

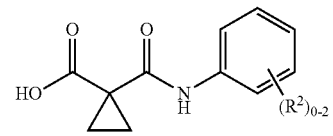

wherein $R^2$ is H, F, Cl, or Br;
comprising
(a) contacting 1,1-cyclopropanedicarboxylic acid with thionyl chloride in a polar aprotic solvent; and
(b) adding

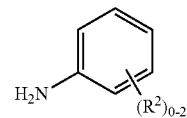

and a tertiary amine base to the mixture of step (a).

In the process, 1,1-cyclopropanedicarboxylic acid is combined with a polar aprotic solvent to form a mixture. In one embodiment, the polar aprotic solvent is selected from the group consisting of dichloromethane, tetrahydrofuran, ethyl acetate, isopropyl acetate, acetone, dimethylformamide, acetonitrile, and dimethylsulfoxide, or combinations thereof. In another embodiment, the polar aprotic solvent is selected form the group consisting of dichloromethane, tetrahydrofuran, ethyl acetate, isopropyl acetate, acetone, dimethylformamide, and acetonitrile, or combinations thereof. In another embodiment, the polar aprotic solvent is selected form the group consisting of dichloromethane, tetrahydrofuran, ethyl acetate, and isopropyl acetate, or combinations thereof. In one embodiment, the polar aprotic solvent is isopropyl acetate.

The volume of polar aprotic solvent used will vary depending on the reaction scale. Typically, approximately 5-10 volumes of polar aprotic acid are used relative to the volume of 1,1-cyclopropanedicarboxylic acid that is used. More typically, 6-9 volumes of polar aprotic acid are used. More typically, 7.5-8.5 volumes of polar aprotic acid are used. Preferably, approximately 8 volumes of the polar aprotic acid are used.

Next, thionyl chloride is added to the mixture comprising 1,1-cyclopropanedicarbopxylic acid and the polar aprotic acid. A molar excess of thionyl chloride is used relative to the number of moles of 1,1-ccyclopropanedicarboxylic acid that is used. Typically, approximately 1.01 to 1.5 molar equivalents of thionyl chloride are used relative to the number of moles of 1,1-cyclopropanedicarbopxylic acid that are used. More typically, approximately 1.01 to 1.2 molar equivalents of thionyl chloride are used. More typically, approximately 1.01 to 1.1 molar equivalents of thionyl chloride are used. More typically, approximately 1.05 molar equivalents of thionyl chloride are used.

The mixture comprising 1,1-cyclopropoanedicarboxylic acid, thionyl chloride, and the polar aprotic solvent is stirred or otherwise agitated for 2 to 24 hours. "Ambient temperature" generally means that no external heating device, such as a heating jacket, heating mantle, or the like, is employed to increase the temperature of the mixture. Typically, the temperature is approximately 23 to 27° C. More typically, the temperature is approximately 24 to 26° C. Typically, the temperature is approximately 25° C. The stirring at room temperature typically continues for approximately 6 to 16 hours. More typically, the stirring continues for approximately 13-15 hours at approximately 25° C.

Next, a mixture of an optionally substituted aniline

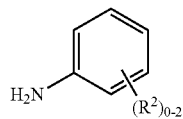

and a tertiary amine base in a polar aprotic solvent is added to the mixture. Typically, the optionally substituted aniline is 4-fluoroaniline.

A molar excess of aniline is used relative to the number of moles of 1,1-cyclopropanedicarboxylic acid. Typically, approximately 1.01 to 1.5 molar equivalents of aniline are used relative to the number of moles of 1,1-cyclopropanedicarbopxylic acid that are used. More typically, approximately 1.01 to 1.2 molar equivalents of aniline are used. More typically, approximately 1.05 to 1.15 molar equivalents of aniline are used. More typically, approximately 1.1 molar equivalents of aniline are used.

The tertiary amine base is typically a trialkyl amine, wherein the alkyl groups are the same or different and may be linear or branched. The use of trialkyl amine bases is well-known to the skilled artisan, and many are commercially available such as triethylamine, di-isopropylethyl amine, or the like. Typically the tertiary amine base is triethyl amine. A molar excess of tertiary amine base is used relative to the number of moles of 1,1-cyclopropanedicarboxylic acid. Typically, approximately 1.01 to 1.5 molar equivalents of tertiary amine base are used relative to the number of moles of 1,1-cyclopropanedicarbopxylic acid that are used. More typically, approximately 1.01 to 1.2 molar equivalents of tertiary amine base are used. More typically, approximately 1.05 to 1.15 molar equivalents of aniline are used. More typically, approximately 1.1 molar equivalents of tertiary amine base are used.

The optionally substituted aniline and tertiary amine base are typically combined in a polar aprotic solvent before they are added to the 1,1-cyclopropanedicarboxylic acid/thionyl chloride/isopropyl acetate mixture. The polar aprotic solvent that is used is typically the same as the solvent that is used to form the 1,1-cyclopropanedicarboxylic acid mixture, and is selected form the group consisting of dichloromethane, tetrahydrofuran, ethyl acetate, isopropyl acetate, acetone, dimethylformamide, acetonitrile, and dimethylsulfoxide, or combinations thereof. In another embodiment, the polar aprotic solvent is selected form the group consisting of dichloromethane, tetrahydrofuran, ethyl acetate, isopropyl acetate, acetone, dimethylformamide, and acetonitrile, or combinations thereof. In another embodiment, the polar aprotic solvent is selected form the group consisting of dichloromethane, tetrahydrofuran, ethyl acetate, and isopropyl acetate, or combinations thereof. In one embodiment, the polar aprotic solvent is isopropyl acetate.

The volume of polar aprotic solvent used to form the aniline/tertiary amine base mixture will vary depending on the reaction scale. Typically, approximately 1-5 volumes of polar aprotic acid are relative to volume of optionally substituted aniline that are used. More typically, 1.5-3 volumes of polar aprotic acid are used. More typically, approximately 2 volumes of polar aprotic acid are used.

The resulting combined mixture is allowed to mix at ambient temperature for 0.5 to 5 hours, and more preferably from 1 to 3 hours. More typically the mixture is allowed to mix for 2 hours.

The mixture, which at this point is typically a slurry comprising Compound A, is then quenched, by treating with a concentrated aqueous base such as 5N aqueous NaOH, KOH, or $K_3PO_4$, or the like. In one embodiment, the base is NaOH. The amount of aqueous base employed to quench the reaction will vary depending the on the reaction scale. For the scale described above, typically approximately 4-6 volumes of 5N NaOH are used. The organic phase of the resulting biphasic mixture is then subsequently extracted with multiple washes of 0.5N NaOH and the aqueous phases are combined. The combined basic extracts are back extracted with an aprotic solvent such as heptane. The combined aqueous phases are then subsequently acidified with an aqueous mineral acid such as HCl, H$_2$SO$_4$, or the like. Typically the acid used is 30 percent HCl in water. The acid is added to the combined aqueous phases to form a slurry. Compound A is then isolated by filtration.

In a further embodiment, a process for preparing a compound of Formula A is provided:

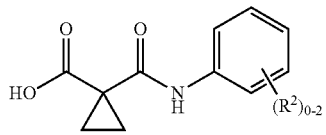
A wherein R$^2$ is H, F, Cl, or Br;
comprising (a) contacting 1,1-cyclopropane dicarboxylic acid with thionyl chloride in isopropyl acetate at room temperature; and (b) adding a mixture comprising

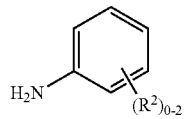

and triethyl amine in isopropyl acetate to the resulting mixture.

In a further embodiment, a process for preparing a compound of Formula A is provided:

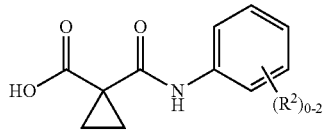
A wherein R$^2$ is H, F, Cl, or Br;
comprising (a) contacting 1,1-cyclopropane dicarboxylic acid with thionyl chloride in isopropyl acetate at room temperature;

(b) adding

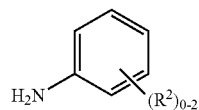

and a triethyl amine to the mixture;

(c) quenching the mixture of step (b) with concentrated aqueous sodium hydroxide;

(d) extracting compound A into dilute aqueous base (e) acidifying the mixture with HCl; and (f) isolating Compound A by filtration.

In a further embodiment, a process for preparing a compound of Formula A-1 is provided:

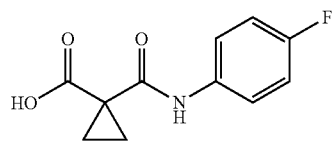
A-1 comprising (a) contacting 1,1-cyclopropane dicarboxylic acid with thionyl chloride in isopropyl acetate at room temperature; and (b) adding a mixture comprising 4-fluoroaniline and a triethyl amine in isopropyl acetate to the resulting mixture.

In a further embodiment, a process for preparing a compound of Formula A-1 is provided:

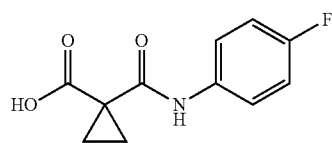
A-1 comprising (a) contacting 1,1-cyclopropane dicarboxylic acid with thionyl chloride in isopropyl acetate at room temperature;

(b) adding a mixture comprising 4-fluoroaniline and a triethyl amine in isopropyl acetate to the resulting mixture;

(c) quenching the mixture with concentrated aqueous sodium hydroxide;

(d) extracting compound A-1 into dilute aqueous base;

(e) acidifying the mixture with HCl; and (f) isolating Compound A by filtration.

In another embodiment, the invention is directed to a process for preparing Compound 1:

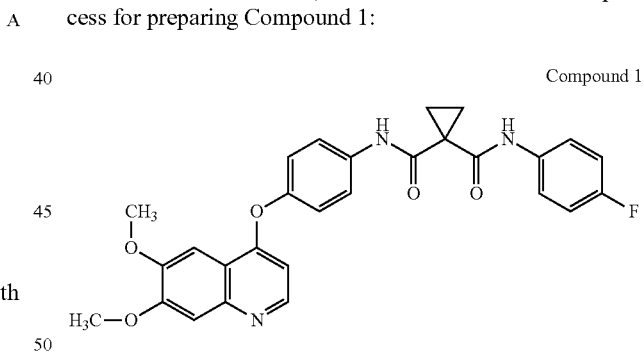
Compound 1 comprising the steps of:

(a) contacting 1,1-cyclopropane dicarboxylic acid with thionyl chloride in a polar aprotic solvent;

(b) adding 4-fluoraniline and triethyl amine to the mixture of step (a) to form a compound of Formula A; and

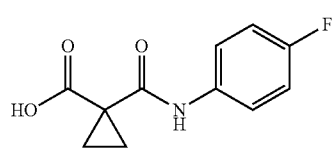
A-1

(c) coupling a compound of Formula A-1 with an amine of Formula B-1 to form Compound 1.

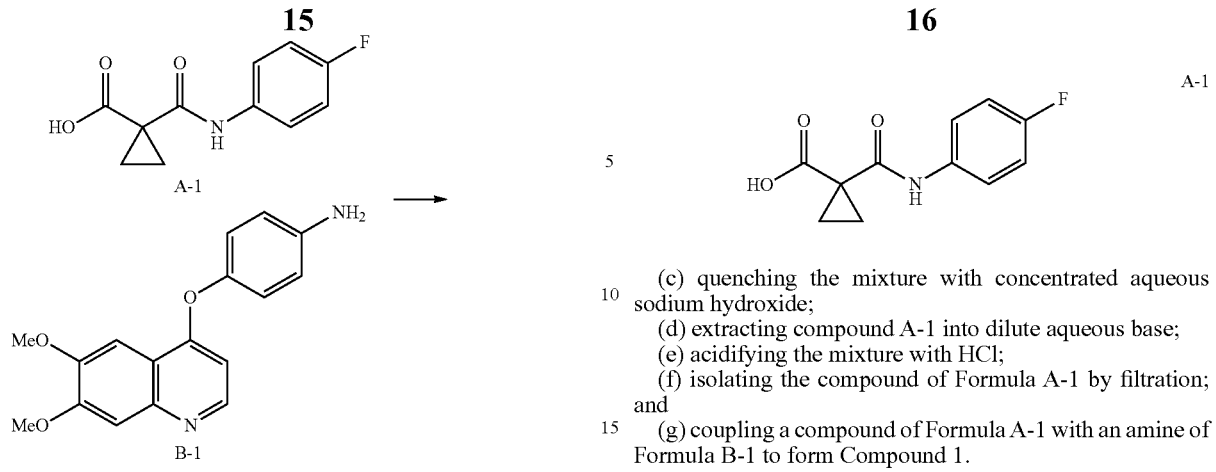

In another embodiment, the invention is directed to a process for preparing Compound 1:

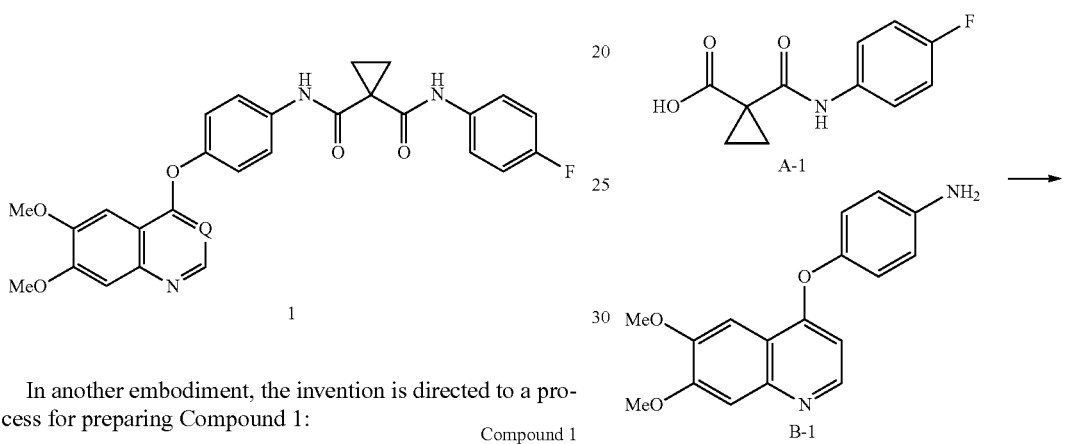

comprising the steps of:

(a) contacting 1,1-cyclopropane dicarboxylic acid with thionyl chloride in a polar aprotic solvent;

(b) adding 4-fluoraniline and triethyl amine to the mixture of step (a) to form a compound of Formula A-1;

(c) quenching the mixture with concentrated aqueous sodium hydroxide;

(d) extracting compound A-1 into dilute aqueous base;

(e) acidifying the mixture with HCl;

(f) isolating the compound of Formula A-1 by filtration; and (g) coupling a compound of Formula A-1 with an amine of Formula B-1 to form Compound 1.

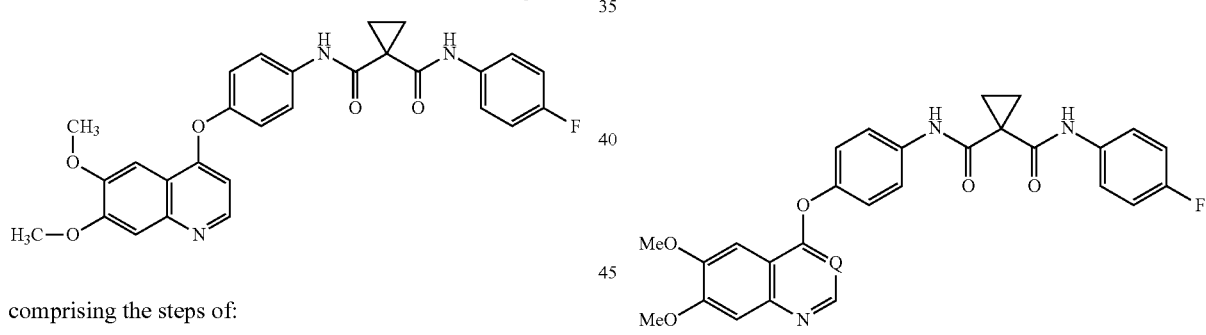

In another embodiment, the invention is directed to a process for preparing Compound 2:

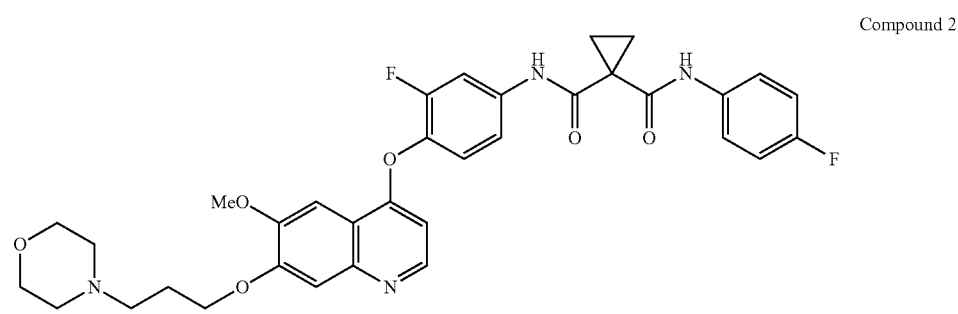 [SMILES: COc1cc2c(Oc3ccc(NC(=O)C4(C(=O)Nc5ccc(F)cc5)CC4)cc3F)ccnc2cc1OCCCN1CCOCC1]

comprising the steps of:

(a) contacting 1,1-cyclopropane dicarboxylic acid with thionyl chloride in a polar aprotic solvent;

(b) adding 4-fluoroaniline and triethyl amine to the mixture of step (a) to form a compound of Formula A-1; and

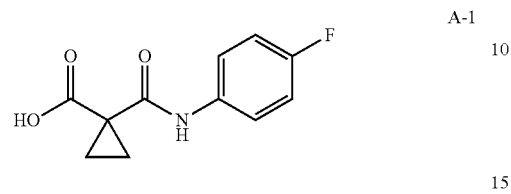

(c) coupling a compound of Formula A-1 with an amine of Formula B-2 to form Compound 2.

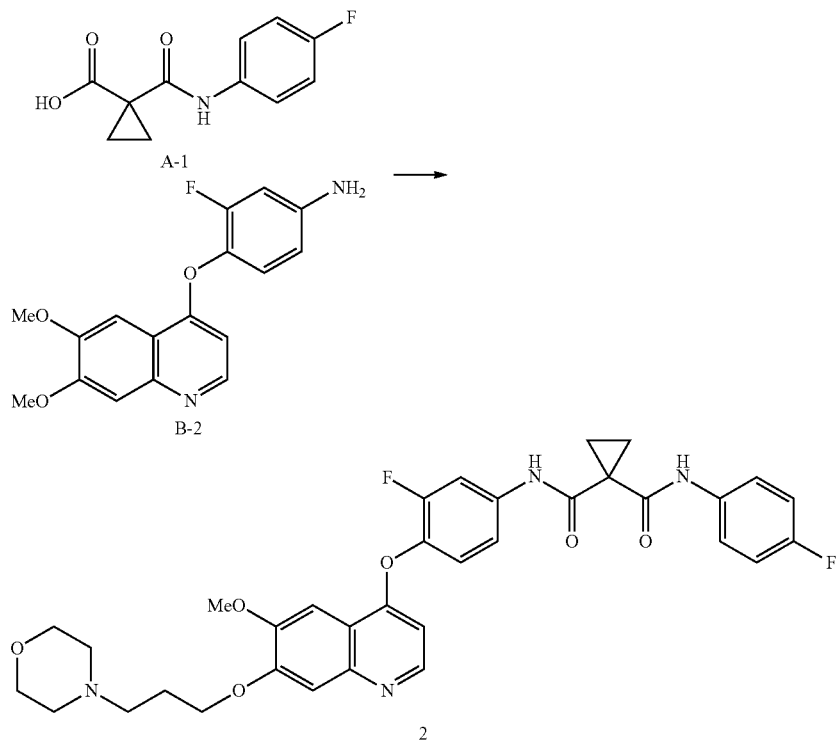

In another embodiment, the invention is directed to a process for preparing Compound 2:

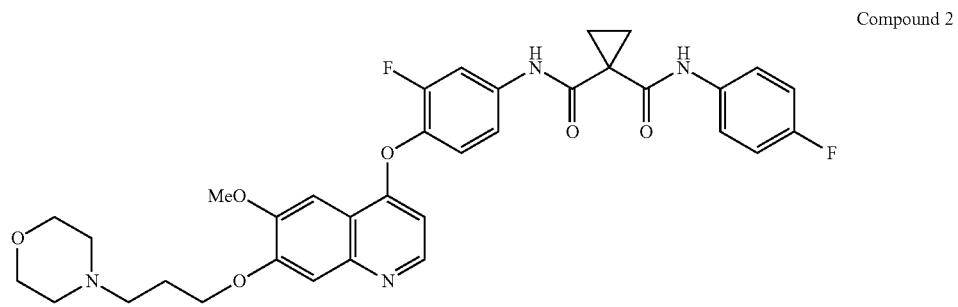 [SMILES: COc1cc2c(Oc3ccc(NC(=O)C4(C(=O)Nc5ccc(F)cc5)CC4)cc3F)ccnc2cc1OCCCN1CCOCC1]

comprising the steps of:

(a) contacting 1,1-cyclopropane dicarboxylic acid with thionyl chloride in a polar aprotic solvent;

(b) adding 4-fluoroaniline and triethyl amine to the mixture of step (a) to form a compound of Formula A-1;

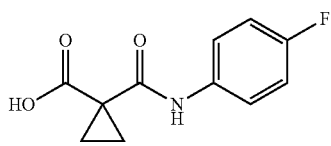 [SMILES: O=C(O)C1(C(=O)Nc2ccc(F)cc2)CC1]

A-1

(c) quenching the mixture with concentrated aqueous sodium hydroxide;

(d) extracting compound A-1 into dilute aqueous base;

(e) acidifying the mixture with HCl;

(f) isolating the compound of Formula A-1 by filtration; and (g) coupling a compound of Formula A-1 with an amine of Formula B-1 to form Compound 2.

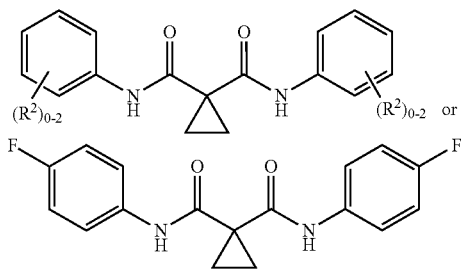

Typically, less than 5 percent, or more typically less than 1 percent, of the bis-amide is formed via the process as claimed herein as evidenced by HPLC analysis of in process control samples. Moreover, the bis-amide, if present, is normally completely removed using the isolation conditions.

Advantageously, the described process also considerably shortens the time taken for the production of a batch of Compound A. Currently, the process for large scale production of Compound A requires several days and subsequent purification by recrystallization. Using the improved process, the typical production time is expected to take one-two days and does not require additional recrystallization.

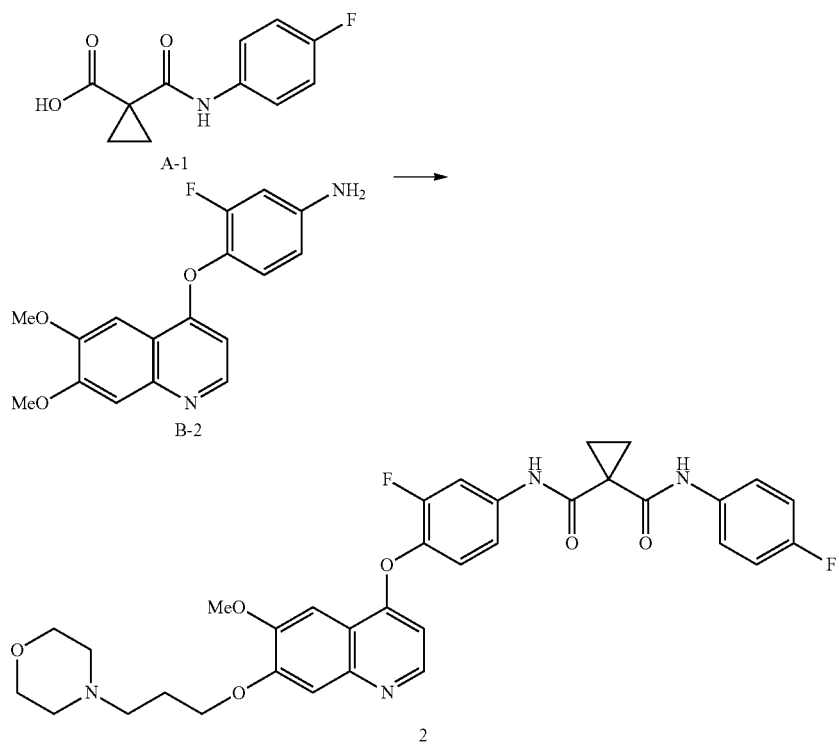

As described herein, reaction of thionyl chloride with 1,1-cyclopropanedicarboxylic acid in a polar aprotic solvent as described herein offers a significant advantage over previous processes in that the reaction is not exothermic. A previous reaction variant wherein $SOCl_2$ was added to a mixture of 1,1-cyclopropanedicarboxylic acid and $Et_3N$ in tetrahydrofuran was very exothermic. The invention process as described herein is noteworthy because carboxylic acids do not normally convert to the corresponding acyl chlorides when treated with $SOCl_2$ at ambient temperature.

The invention process as disclosed herein is highly selective for formation of the mono-amidation product Compound A over the bis-amide.

EXPERIMENTAL PROCEDURES

The invention is illustrated further by the following examples in Scheme 1 and the description thereof, which are not to be construed as limiting the invention in scope or spirit to the specific procedures described in them. Those having skill in the art will recognize that the starting materials may be varied and additional steps employed to produce compounds encompassed by the invention, as demonstrated by the following examples. Those skilled in the art will also recognize that it may be necessary to utilize different solvents or reagents to achieve some of the above transformations.

Unless otherwise specified, all reagents and solvents are of standard commercial grade and are used without further purification. The appropriate atmosphere to run the reaction under, for example, air, nitrogen, argon, and the like, will be apparent to those skilled in the art.

Preparation of 1-(4-Fluorophenylcarbamoyl)cyclopropanecarboxylic acid (Compound A-1)

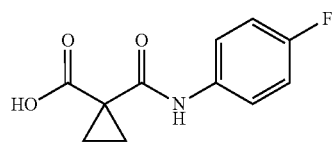

The starting 1,1-cyclopropanedicarboxylic acid was treated with thionyl chloride (1.05 equivalents) in approximately 8 volumes of isopropyl acetate at 25° C. for 5 hours. The resulting mixture was then treated with a solution of 4-fluoroaniline (1.1 equivalents) and triethylamine (1.1 equivalents) in isopropyl acetate (2 volumes) over 1 hour. The product slurry was quenched with 5N NaOH solution (5 volumes) and the aqueous phase is discarded. The organic phase was extracted with 0.5N NaOH solution (10 volumes) and the basic extract was washed with heptane (5 volumes) and subsequently acidified with 30% HCl solution to give a slurry. Compound A-1 was isolated by filtration.

Compound A-1 was prepared on a 1.00 kg scale using 1,1-cyclopropanedicarboxylic acid as the limiting reagent to furnish 1.32 kg of Compound A-1 (77% isolated yield; 84% mass balance) with 99.92% purity (HPLC) and 100.3% assay.

Preparation of N-(4-{[6,7-bis(methyloxy)quinolin-4-yl]oxy}phenyl)-N'-(4-fluorophenyl)cyclopropane-1,1-dicarboxamide (Compound 1) and the (L)-malate salt thereof A synthetic route that can be used for the preparation of N-(4-{[6,7-bis(methyloxy)quinolin-4-yl]oxy}phenyl)-N'-(4-fluorophenyl)cyclopropane-1,1-dicarboxamide and the (L)-malate salt thereof is depicted in Scheme 1.

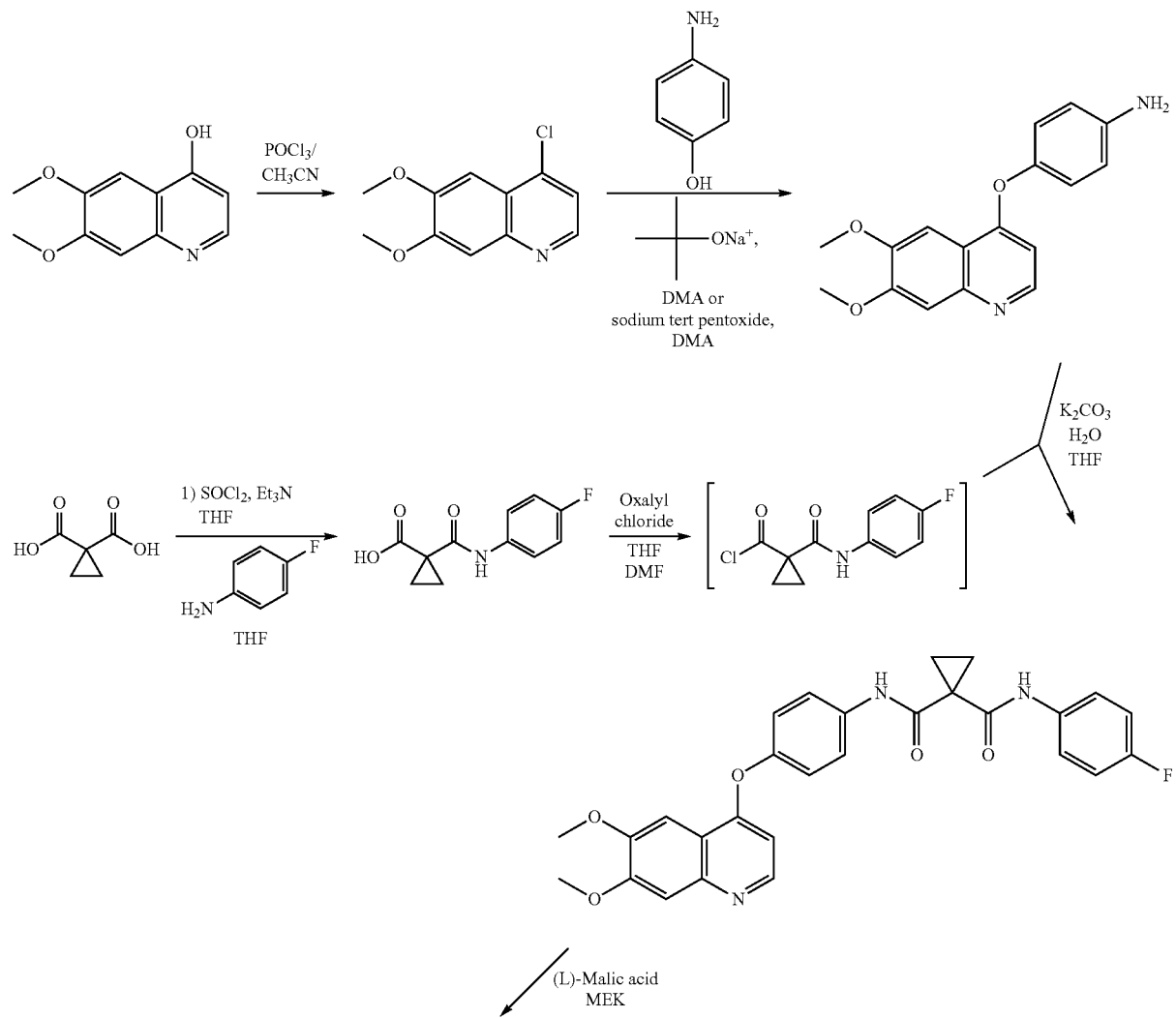

Scheme 1

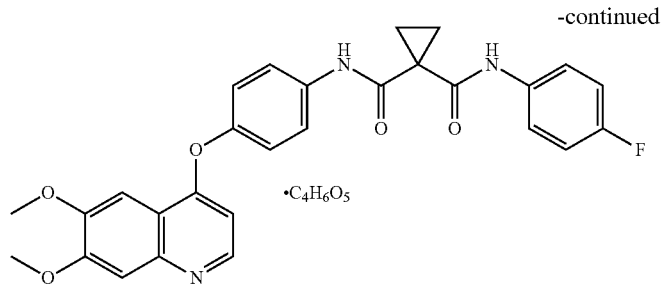
Another synthetic route that can be used for the preparation of N-(4-{[6,7-bis(methyloxy)quinolin-4-yl]oxy}phenyl)-N'-(4-fluorophenyl)cyclopropane-1,1-dicarboxamide and the (L)-malate salt thereof is depicted in Scheme 2.
Preparation of 4-Chloro-6,7-dimethoxy-quinoline
A reactor was charged sequentially with 6,7-dimethoxy-quinoline-4-ol (47.0 kg) and acetonitrile (318.8 kg). The
Scheme 2
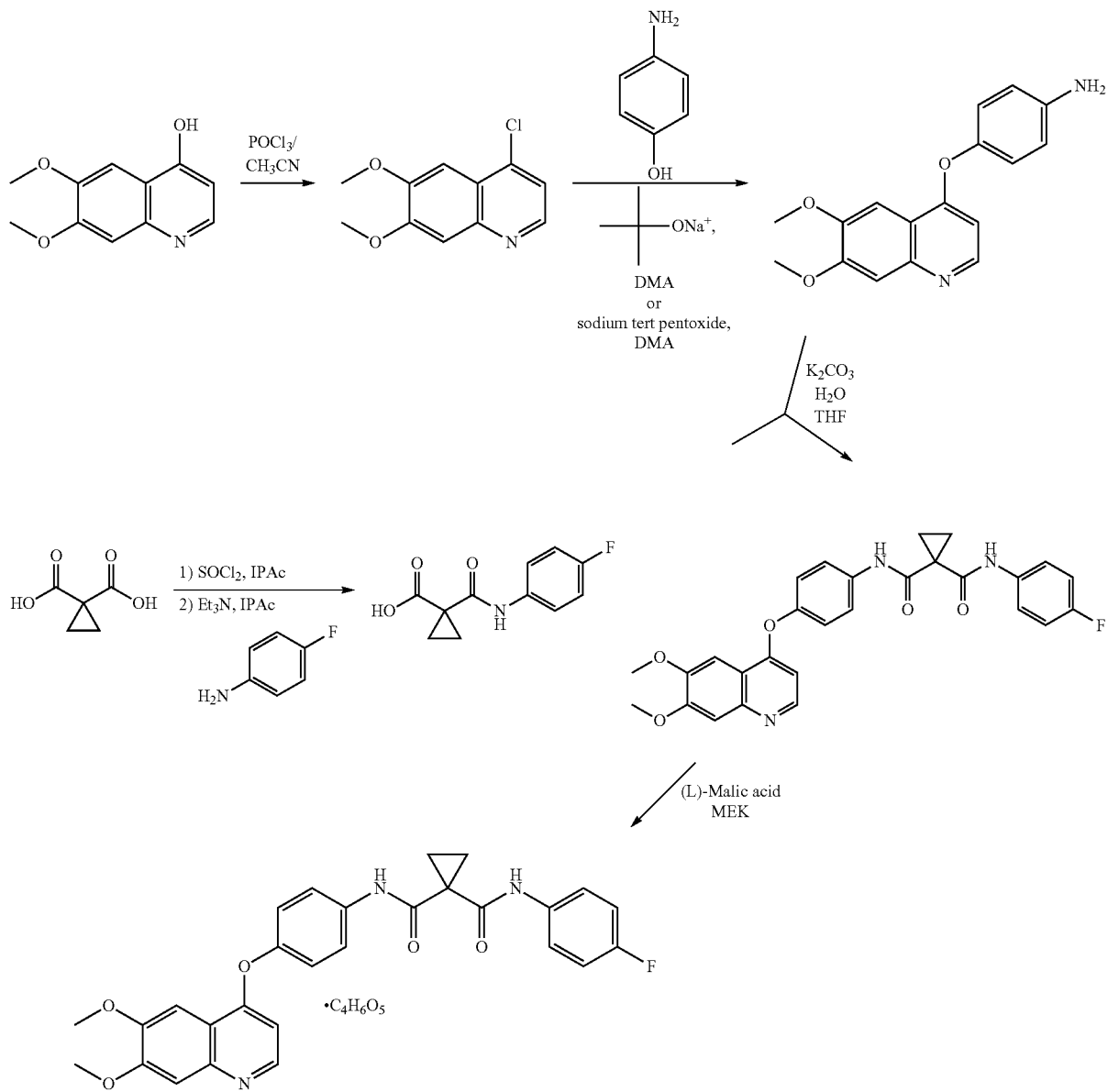

resulting mixture was heated to approximately 60° C. and phosphorus oxychloride (POCl$_3$, 130.6 kg) was added. After the addition of POCl$_3$, the temperature of the reaction mixture was raised to approximately 77° C. The reaction was deemed complete (approximately 13 hours) when less than 3% of the starting material remained (in-process high-performance liquid chromatography [HPLC] analysis). The reaction mixture was cooled to approximately 2 to 7° C. and then quenched into a chilled solution of dichloromethane (DCM, 482.8 kg), 26% NH$_4$OH (251.3 kg), and water (900 L). The resulting mixture was warmed to approximately 20 to 25° C., and phases were separated. The organic phase was filtered through a bed of AW hyflo super-cel NF (Celite; 5.4 kg), and the filter bed was washed with DCM (118.9 kg). The combined organic phase was washed with brine (282.9 kg) and mixed with water (120 L). The phases were separated and the organic phase was concentrated by vacuum distillation with the removal of solvent (approximately 95 L residual volume). DCM (686.5 kg) was charged to the reactor containing organic phase and concentrated by vacuum distillation with the removal of solvent (approximately 90 L residual volume). Methyl t-butyl ether (MTBE, 226.0 kg) was then charged and the temperature of the mixture was adjusted to −20 to −25° C. and held for 2.5 hours resulting in solid precipitate, which was then filtered and washed with n-heptane (92.0 kg), and dried on a filter at approximately 25° C. under nitrogen to afford the title compound (35.6 kg).

Preparation of
4-(6,7-Dimethoxy-quinoline-4-yloxy)-phenylamine

4-Aminophenol (24.4 kg) dissolved in N,N-dimethylacetamide (DMA, 184.3 kg) was charged to a reactor containing 4-chloro-6,7-dimethoxyquinoline (35.3 kg), sodium t-butoxide (21.4 kg), and DMA (167.2 kg) at 20-25° C. This mixture was then heated to 100-105° C. for approximately 13 hours. After the reaction was deemed complete as determined using in-process HPLC analysis (less than 2% starting material remaining), the reactor contents were cooled at 15 to 20° C. and water (pre-cooled, 2 to 7° C., 587 L) charged at a rate to maintain 15 to 30° C. temperature. The resulting solid precipitate was filtered, washed with a mixture of water (47 L) and DMA (89.1 kg) and finally with water (214 L). The filter cake was then dried at approximately 25° C. on filter to yield crude 4-(6,7-dimethoxy-quinoline-4-yloxy)-phenylamine (59.4 kg wet, 41.6 kg dry calculated based on LOD). Crude 4-(6,7-dimethoxy-quinoline-4-yloxy)-phenylamine was refluxed (approximately 75° C.) in a mixture of tetrahydrofuran (THF, 211.4 kg) and DMA (108.8 kg) for approximately 1 hour and then cooled to 0 to 5° C. and aged for approximately 1 hour after which time the solid was filtered, washed with THF (147.6 kg) and dried on a filter under vacuum at approximately 25° C. to yield 4-(6,7-dimethoxy-quinoline-4-yloxy)-phenylamine (34.0 kg).

Alternative Preparation of
4-(6,7-Dimethoxy-quinoline-4-yloxy)-phenylamine 4-chloro-6,7-dimethoxyquinoline (34.8 kg) and 4-Aminophenol (30.8 kg) and sodium tert pentoxide (1.8 equivalents) 88.7 kg, 35 weight percent in THF) were charged to a reactor, followed by N,N-dimethylacetamide (DMA, 293.3 kg). This mixture was then heated to 105 to 115° C. for approximately 9 hours. After the reaction was deemed complete as determined using in-process HPLC analysis (less than 2% starting material remaining), the reactor contents were cooled at 15 to 25° C. and water (315 kg) was added over a two hour period while maintaining the temperature between 20 and 30° C. The reaction mixture was then agitated for an additional hour at 20 to 25° C. The crude product was collected by filtration and washed with a mixture of 88 kg water and 82.1 kg DMA, followed by 175 kg water. The product was dried on a filter drier for 53 hours. The LOD showed less than 1% w/w.

In an alternative procedure, 1.6 equivalents of sodium tert-pentoxide were used and the reaction temperature was increased from 110 to 120° C. In addition, the cool down temperature was increased to 35 to 40° C. and the starting temperature of the water addition was adjusted to 35 to 40° C., with an allowed exotherm to 45° C.

Preparation of
1-(4-Fluoro-phenylcarbamoyl)-cyclopropanecarbonyl chloride

Oxalyl chloride (12.6 kg) was added to a solution of 1-(4-fluoro-phenylcarbamoyl)-cyclopropanecarboxylic acid (22.8 kg) in a mixture of THF (96.1 kg) and N,N-dimethylformamide (DMF; 0.23 kg) at a rate such that the batch temperature did not exceed 25° C. This solution was used in the next step without further processing.

Alternative Preparation of
1-(4-Fluoro-phenylcarbamoyl)-cyclopropanecarbonyl chloride A reactor was charged with 1-(4-fluoro-phenylcarbamoyl)-cyclopropanecarboxylic acid (35 kg), 344 g DMF, and 175 kg THF. The reaction mixture was adjusted to 12 to 17° C. and then to the reaction mixture was charged 19.9 kg of oxalyl chloride over a period of 1 hour. The reaction mixture was left stirring at 12 to 17° C. for 3 to 8 hours. This solution was used in the next step without further processing.

Preparation of cyclopropane-1,1-dicarboxylic acid
[4-(6,7-dimethoxy-quinoline-4-yloxy)-phenyl]-amide(4-fluoro-phenyl)-amide The solution from the previous step containing 1-(4-fluoro-phenylcarbamoyl)-cyclopropanecarbonyl chloride was added to a mixture of compound 4-(6,7-dimethoxy-quinoline-4-yloxy)-phenylamine (23.5 kg) and potassium carbonate (31.9 kg) in THF (245.7 kg) and water (116 L) at a rate such that the batch temperature did not exceed 30° C. When the reaction was complete (in approximately 20 minutes), water (653 L) was added. The mixture was stirred at 20 to 25° C. for approximately 10 hours, which resulted in the precipitation of the product. The product was recovered by filtration, washed with a pre-made solution of THF (68.6 kg) and water (256 L), and dried first on a filter under nitrogen at approximately 25° C. and then at approximately 45° C. under vacuum to afford the title compound (41.0 kg, 38.1 kg, calculated based on LOD).

Alternative Preparation of cyclopropane-1,1-dicarboxylic acid [4-(6,7-dimethoxy-quinoline-4-yloxy)-phenyl]-amide(4-fluoro-phenyl)-amide A reactor was charged with 4-(6,7-dimethoxy-quinoline-4-yloxy)-phenylamine (35.7 kg, 1 equivalent), followed by 412.9 kg THF. To the reaction mixture was charged a solution of 48.3 K$_2$CO$_3$ in 169 kg water. The acid chloride solution of described in the Alternative Preparation of 1-(4-Fluoro-phenylcarbamoyl)-cyclopropanecarbonyl chloride above was transferred to the reactor containing 4-(6,7-dimethoxy-quinoline-4-yloxy)-phenylamine while maintaining the temperature between 20 to 30° C. over a minimum of two hours. The reaction mixture was stirred at 20 to 25° C. for a minimum of three hours. The reaction temperature was then adjusted to 30 to 25° C., and the mixture was agitated. The agitation was stopped and the phases of the mixture were allowed to separate. The lower aqueous phase was removed and discarded. To the remaining upper organic phase was added 804 kg water. The reaction was left stirring at 15 to 25° C. for a minimum of 16 hours.

The product precipitated. The product was filtered and washed with a mixture of 179 kg water and 157.9 THF in two portions. The crude product was dried under a vacuum for at least two hours. The dried product was then taken up in 285.1 kg THF. The resulting suspension was transferred to reaction vessel and agitated until the suspension became a clear (dissolved) solution, which required heating to 30 to 35° C. for approximately 30 minutes. 456 kg water was then added to the solution, as well as 20 kg SDAG-1 ethanol (ethanol denatured with methanol over two hours). The mixture was agitated at 15 to 25° C. for at least 16 hours. The product was filtered and washed with a mixture of 143 kg water and 126.7 THF in two portions. The product was dried at a maximum temperature set point of 40° C.

In an alternative procedure, the reaction temperature during acid chloride formation was adjusted to 10 to 15° C. The recrystallization temperature was changed from 15 to 25° C. to 45 to 50° C. for 1 hour and then cooled to 15 to 25° C. over 2 hours.

Preparation of cyclopropane-1,1-dicarboxylic acid [4-(6,7-dimethoxy-quinoline-4-yloxy)-phenyl]-amide(4-fluoro-phenyl)-amide, XL184 (L) malate salt Cyclopropane-1,1-dicarboxylic acid [4-(6,7-dimethoxy-quinoline-4-yloxy)-phenyl]-amide(4-fluoro-phenyl)-amide (1-5; 13.3 kg), L-malic acid (4.96 kg), methyl ethyl ketone (MEK; 188.6 kg) and water (37.3 kg) were charged to a reactor and the mixture was heated to reflux (approximately 74° C.) for approximately 2 h. The reactor temperature was reduced to 50 to 55° C., and the reactor contents were filtered. These sequential steps described above were repeated two more times starting with similar amounts of 1-5 (13.3 kg), L-Malic acid (4.96 kg), MEK (198.6 kg), and water (37.2 kg). The combined filtrate was azeotropically dried at atmospheric pressure using MEK (1133.2 kg) (approximate residual volume 711 L; KF<0.5% w/w) at approximately 74° C. The temperature of the reactor contents was reduced to 20 to 25° C. and held for approximately 4 hours, resulting in solid precipitate which was filtered, washed with MEK (448 kg) and dried under vacuum at 50° C. to afford the title compound (45.5 kg).

Alternative Preparation of cyclopropane-1,1-dicarboxylic acid [4-(6,7-dimethoxy-quinoline-4-yloxy)-phenyl]-amide(4-fluoro-phenyl)-amide, (L) malate salt Cyclopropane-1,1-dicarboxylic acid [4-(6,7-dimethoxy-quinoline-4-yloxy)-phenyl]-amide(4-fluoro-phenyl)-amide (47.9 kg), L-malic acid (17.2), 658.2 kg methyl ethyl ketone, and 129.1 kg water (37.3 kg) were charged to a reactor and the mixture was heated 50 to 55° C. for approximately 1 to 3 hours, and then at 55 to 60° C. for an additional 4 to 5 hours. The mixture was clarified by filtration through a 1 μm cartridge. The reactor temperature was adjusted to 20 to 25° C. and vacuum distilled with a vacuum at 150 to 200 mm Hg with a maximum jacket temperature of 55° C. to the volume range of 558 to 731 L.

The vacuum distillation was performed two more times with the charge of 380 kg and 380.2 kg methyl ethyl ketone, respectively. After the third distillation, the volume of the batch was adjusted to 18 v/w of Cyclopropane-1,1-dicarboxylic acid [4-(6,7-dimethoxy-quinoline-4-yloxy)-phenyl]-amide(4-fluoro-phenyl)-amide by charging 159.9 kg methyl ethyl ketone to give a total volume of 880 L. An additional vacuum distillation was carried out by adjusting 245.7 methyl ethyl ketone. The reaction mixture was left with moderate agitation at 20 to 25° C. for at least 24 hours. The product was filtered and washed with 415.1 kg methyl ethyl ketone in three portions. The product was dried under a vacuum with the jacket temperature set point at 45° C.

In an alternative procedure, the order of addition was changes so that a solution of 17.7 kg L-malic acid dissolved in 129.9 kg water was added to Cyclopropane-1,1-dicarboxylic acid [4-(6,7-dimethoxy-quinoline-4-yloxy)-phenyl]-amide (4-fluoro-phenyl)-amide (48.7 kg) in methyl ethyl ketone (673.3 kg).

Preparation of Compound 2

Compound 2 was prepared as provided in Scheme 3 and the accompanying experimental examples.

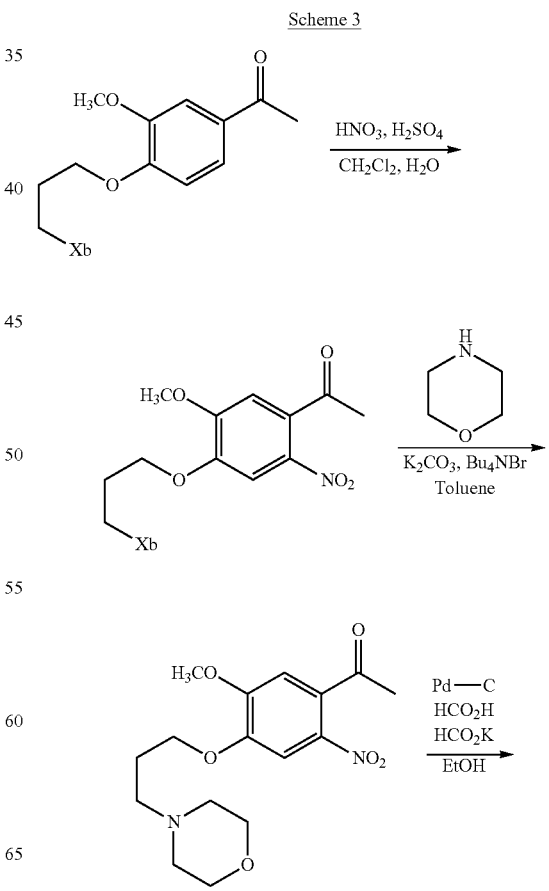

Scheme 3

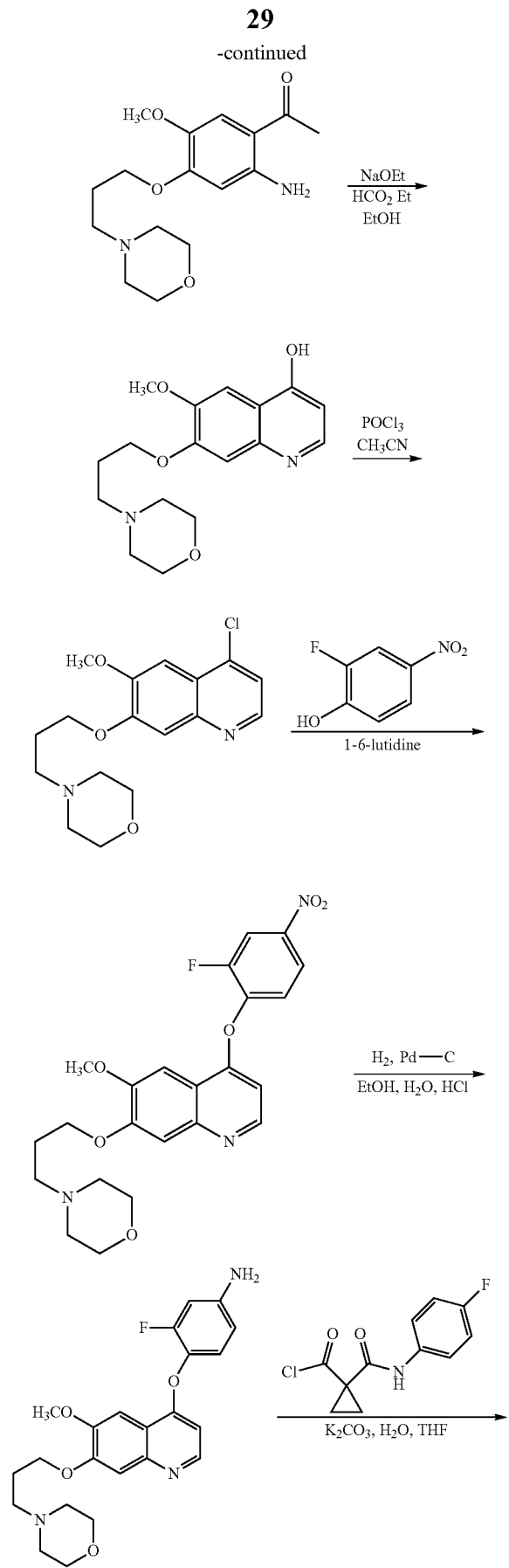

In Scheme 3, Xb is Br or Cl. For the names of the intermediates described within the description of Scheme 3 below, Xb is referred to as halo, wherein this halo group for these intermediates is meant to mean either Br or Cl.

Preparation of 1-[5 methoxy-4 (3-halo propoxy)-2 nitro-phenyl]-ethanone

Water (70 L) was charged to the solution of 1-[4-(3-halo propoxy)-3-methoxy phenyl]ethanone (both the bromo and the chloro compound are commercially available). The solution was cooled to approximately 4° C. Concentrated sulfuric acid (129.5 kg) was added at a rate such that the batch temperature did not exceed approximately 18° C. The resulting solution was cooled to approximately 5° C. and 70 percent nitric acid (75.8 kg) was added at a rate such that the batch temperature did not exceed approximately 10° C. Methylene chloride, water, and ice were charged to a separate reactor. The acidic reaction mixture was then added into this mixture. The methylene chloride layer was separated, and the aqueous layer was back extracted with methylene chloride. The combined methylene chloride layers were washed with aqueous potassium bicarbonate solution and concentrated by vacuum distillation. 1-Butanol was added and the mixture was again concentrated by vacuum distillation. The resulting solution was stirred at approximately 20° C., during which time the product crystallized. The solids were collected by filtration, washed with 1-butanol to afford compound the title compound, which was isolated as a solvent wet cake, and used directly in the next step. $^1$H NMR (400 MHz, DMSO-d6): δ 7.69 (s, 1H), 7.24 (s, 1H); 4.23 (m, 2H); 3.94 (s, 3H); 3.78 (t)-3.65 (t) (2H), 2.51 (s, 3H), 2.30-2.08 (m, 2H) LC/MS Calcd for [M(Cl)+H]$^+$ 288.1. found 288.0; Calcd for [M(Br)+H]$^+$ 332.0, 334.0. found 331.9, 334.0.

Preparation of 1-[5-methoxy-4-(3-morpholin-4-yl-propoxy)-2-nitro-phenyl]-ethanone The solvent wet cake isolated in the previous step was dissolved in toluene. A solution of sodium iodide (67.9 kg) and potassium carbonate (83.4 kg) was added to this solution, followed by tetrabutylammonium bromide (9.92 kg) and morpholine (83.4 kg). The resulting 2 phase mixture was heated to approximately 85° C. for approximately 9 hours. The mixture was then cooled to ambient temperature. The organic layer was removed. The aqueous layer was back extracted with toluene. The combined toluene layers were washed sequentially with two portions of saturated aqueous sodium thiosulfate followed by two portions of water. The resulting solution of the title compound was used in the next step without further processing. $^1$H NMR (400 MHz, DMSO-d6): δ 7.64 (s, 1H), 7.22 (s, 1H), 4.15 (t, 2H), 3.93 (s, 3H), 3.57

(t, 4H), 2.52 (s, 3H), 2.44-2.30 (m, 6H), 1.90 (quin, 2H); LC/MS Calcd for [M+H]+ 339.2. found 339.2.

Preparation of 1-[2-amino-5-methoxy-4-(3-morpholin-4-yl-propoxy)-phenyl]-ethanone The solution from the previous step was concentrated under reduced pressure to approximately half of the original volume. Ethanol and 10 percent Pd/C (50 percent water wet, 5.02 kg) were added; the resulting slurry was heated to approximately 48° C., and an aqueous solution of formic acid (22.0 kg) and potassium formate (37.0 kg) was added. When the addition was complete and the reaction deemed complete by thin layer chromatography (TLC), water was added to dissolve the by-product salts. The mixture was filtered to remove the insoluble catalyst. The filtrate was concentrated under reduced pressure and toluene was added. The mixture was made basic (pH of approximately 10) by the addition of aqueous potassium carbonate. The toluene layer was separated and the aqueous layer was back extracted with toluene. The combined toluene phases were dried over anhydrous sodium sulfate. The drying agent was removed by filtration and the resulting solution was used in the next step without further processing. $^1$H NMR (400 MHz, DMSO-d6): δ 7.11 (s, 1H)-7.01 (br s, 2H), 6.31 (s, 1H), 3.97 (t, 2H), 3.69 (s, 3H), 3.57 (t, 4H), 2.42 (s, 3H), 2.44-2.30 (m, 6H), 1.91 (quin, 2H LC/MS Calcd for [M+H]+ 309.2. found 309.1.

Preparation of 6-methoxy-7-(3-morpholin-4-yl-propoxy)-quinolin-4-ol, sodium salt A solution of sodium ethoxide (85.0 kg) in ethanol and ethyl formate (70.0 kg) was added to the solution from the previous step. The mixture was warmed to approximately 44° C. for approximately 3 hours. The reaction mixture was cooled to approximately 25° C. Methyl t-butyl ether (MTBE) was added which caused the product to precipitate. The product was collected by filtration and the cake was washed with MTBE and dried under reduced pressure at ambient temperature. The dried product was milled through a mesh screen to afford 60.2 kg of the title compound. $^1$H NMR (400 MHz, DMSO-d6): δ 11.22 (br s, 1H), 8.61 (d, 1H), 7.55 (s, 1H), 7.54 (s, 1H), 7.17 (d, 1H), 4.29 (t, 2H), 3.99 (m, 2H), 3.96 (s, 3H), 3.84 (t, 2H), 3.50 (d, 2H), 3.30 (m, 2H), 3.11 (m, 2H), 2.35 (m, 2H), LC/MS Calcd for [M+H]+ 319.2. found 319.1.

Preparation of 4-chloro-6-methoxy-7-(3 morpholin-4-yl)-quinoline

Phosphorous oxychloride (26.32 kg) was added to a solution of 6-methoxy-7-(3-morpholin-4-yl-propoxy)-quinolin-4-ol (5.00 kg) in acetonitrile that was heated to 50 to 55° C. When the addition was complete, the mixture was heated to reflux (approximately 82° C.) and held at that temperature, with stirring for approximately 18 hours, at which time it was sampled for in process HPLC analysis. The reaction was considered complete when no more than 5 percent starting material remained. The reaction mixture was then cooled to 20 to 25° C. and filtered to remove solids. The filtrate was then concentrated to a residue. Acetonitrile was added and the resulting solution was concentrated to a residue. Methylene chloride was added to the residue and the resulting solution was quenched with a mixture of methylene chloride and aqueous ammonium hydroxide. The resulting two phase mixture was separated, and the aqueous layer was back extracted with methylene chloride. The combined methylene chloride solutions were dried over anhydrous magnesium sulfate, filtered, and concentrated to a solid. The solids were dried at 30 to 40° C. under reduced pressure to afford the title compound (1.480 kg). $^1$H NMR (400 MHz, DMSO-d6): δ 8.61 (d, 1H), 7.56 (d, 1H), 7.45 (s, 1H), 7.38 (s, 1H), 4.21 (t, 2H), 3.97 (s, 3H), 3.58 (m, 2H), 2.50-2.30 (m, 6H), 1.97 (quin, 2H) LC/MS Calcd for [M+H]+ 458.2. found 458.0.

Preparation of 4-(2-fluoro-4-nitro-phenoxy)-6-methoxy-7-(3-morpholin-4-yl propoxy)quinoline A solution of 4-chloro-6-methoxy-7-(3 morpholin-4-yl)-quinoline (2.005 kg, 5.95 mol) and 2 fluoro-4-nitrophenol (1.169 kg, 7.44 mol) in 2,6-lutidine was heated to 140 to 145° C., with stirring, for approximately 2 hours, at which time it was sampled for in process HPLC analysis. The reaction was considered complete when less than 5 percent starting material remained. The reaction mixture was then cooled to approximately 75° C., and water was added. Potassium carbonate was added to the mixture, which was then stirred at ambient temperature overnight. The solids that precipitated were collected by filtration, washed with aqueous potassium carbonate, and dried at 55 to 60° C. under reduced pressure to afford the title compound (1.7 kg). $^1$H NMR (400 MHz, DMSO-d6): δ 8.54 (d, 1H), 8.44 (dd, 1H), 8.18 (m, 1H), 7.60 (m, 1H), 7.43 (s, 1H), 7.42 (s, 1H), 6.75 (d, 1H), 4.19 (t, 2H), 3.90 (s, 3H), 3.56 (t, 4H), 2.44 (t, 2H), 2.36 (m, 4H), 1.96 (m, 2H). LC/MS Calcd for [M+H]+ 337.1, 339.1. found 337.0, 339.0.

Preparation of 3-fluoro-4-[6-methoxy-7-(3-morpholin-4-yl-propoxy)-quinolin-4-yloxy]-phenylamine A reactor containing 4-(2-fluoro-4-nitro-phenoxy)-6-methoxy-7-(3-morpholin-4-yl propoxy)quinoline (2.5 kg) and 10 percent palladium on carbon (50 percent water wet, 250 g) in a mixture of ethanol and water containing concentrated hydrochloric acid (1.5 L) was pressurized with hydrogen gas (approximately 40 psi). The mixture was stirred at ambient temperature. When the reaction was complete (typically 2 hours), as evidenced by in process HPLC analysis, the hydrogen was vented and the reactor inerted with argon. The reaction mixture was filtered through a bed of Celite® to remove the catalyst. Potassium carbonate was added to the filtrate until the pH of the solution was approximately 10. The resulting suspension was stirred at 20 to 25° C. for approximately 1 hour. The solids were collected by filtration, washed with water, and dried at 50 to 60° C. under reduced pressure to afford the title compound (1.164 kg). $^1$H NMR (400 MHz, DMSO-d6): δ 8.45 (d, 1H), 7.51 (s, 1H), 7.38 (s, 1H), 7.08 (t, 1H), 6.55 (dd, 1H), 6.46 (dd, 1H), 6.39 (dd, 1H), 5.51 (br. s, 2H), 4.19 (t, 2H), 3.94 (s, 3H), 3.59 (t, 4H), 2.47 (t, 2H), 2.39 (m, 4H), 1.98 (m, 2H). LC/MS Calcd for [M+H]+ 428.2. found 428.1.

Preparation of 1-(4-fluoro-phenylcarbamoyl)-cyclopropanecarbonylchloride

Oxalyl chloride (291 mL) was added slowly to a cooled (approximately 5° C.) solution of 1-(4-fluoro-phenylcarbamoyl)-cyclopropanecarboxylic acid in THF at a rate such that the batch temperature did not exceed 10° C. When the addition was complete, the batch was allowed to warm to ambient temperature and held with stirring for approximately 2 hours, at which time in process HPLC analysis indicated the reaction was complete. The solution was used in the next step without further processing.

Preparation of cyclopropane-1,1-dicarboxylic acid {3-fluoro-4-[6-methoxy-7-(3-morpholin-4-yl-propoxy)-quinolin-4-ylamino]phenyl}-amide-(4 fluorophenyl)-amide The solution from the previous step was added to a mixture of 3-fluoro-4-[6-methoxy-7-(3-morpholin-4-yl-propoxy)-quinolin-4-yloxy]-phenylamine (1160 kg) and potassium carbonate (412.25 g) in THF and water at a rate such that the batch temperature was maintained at approximately 15 to 21° C. When the addition was complete, the batch was warmed to ambient temperature and held with stirring for approximately 1 hour, at which time in process HPLC analysis indicated the reaction was complete. Aqueous potassium carbonate solution and isopropyl acetate were added to the batch. The resulting two phase mixture was stirred, and then the phases were allowed to separate. The aqueous phase was back extracted with isopropyl acetate. The combined isopropyl acetate layers were washed with water followed by aqueous sodium chloride and then slurried with a mixture of magnesium sulfate and activated carbon. The slurry was filtered over Celite®, and the filtrate was concentrated to an oil at approximately 30° C. under vacuum to afford the title compound, which was carried into the next step without further processing. $^1$H NMR (400 MHz, DMSO-d6): δ 10.41 (s, 1H), 10.03 (s, 1H), 8.47 (d, 1H), 7.91 (dd, 1H), 7.65 (m, 2H), 7.53 (m, 2H), 7.42 (m, 2H), 7.16 (t, 2H), 6.41 (d, 1H), 4.20 (t, 2H), 3.95 (s, 3H), 3.59 (t, 4H), 2.47 (t, 2H), 2.39 (m, 4H), 1.98 (m, 2H), 1.47 (m, 4H). LC/MS Calcd for [M+H]$^+$ 633.2. found 633.1.

Preparation of the bisphosphate salt of cyclopropane-1,1-dicarboxylic acid {3-fluoro-4-[6-methoxy-7-(3-morpholin-4-yl-propoxy)-quinolin-4-ylamino]phenyl}-amide(4-fluoro-phenyl)-amide Cyclopropane-1,1-dicarboxylic acid {3-fluoro-4-[6-methoxy-7-(3-morpholin-4-yl-propoxy)-quinolin-4-ylamino]phenyl}-amide-(4 fluoro phenyl)-amide from the previous step was dissolved in acetone and water. Phosphoric acid (85%, 372.48 g) was added at a rate such that the batch temperature did not exceed 30° C. The batch was maintained at approximately 15 to 30° C. with stirring for 1 hour, during which time the product precipitated. The solids were collected by filtration, washed with acetone, and dried at approximately 60° C. under vacuum to afford the title compound (1.533 kg). The title compound has a c-Met IC$_{50}$ value of less than 50 nM. The bisphosphate salt is not shown in scheme 3. $^1$H NMR (400 MHz, DMSO-d6): (diphosphate) δ 10.41 (s, 1H), 10.02 (s, 1H), 8.48 (d, 1H), 7.93 (dd, 1H), 7.65 (m, 2H), 7.53 (d, 2H), 7.42 (m, 2H), 7.17 (m, 2H), 6.48 (d, 1H), 5.6 (br s, 6H), 4.24 (t, 2H), 3.95 (s, 3H), 3.69 (bs, 4H), 2.73 (bs, 6H), 2.09 (t, 2H), 1.48 (d, 4H).

Procedure for Direct Coupling

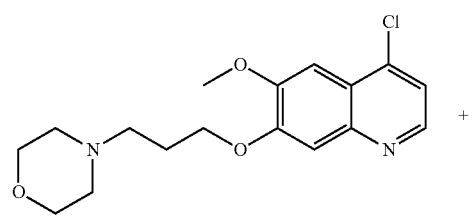

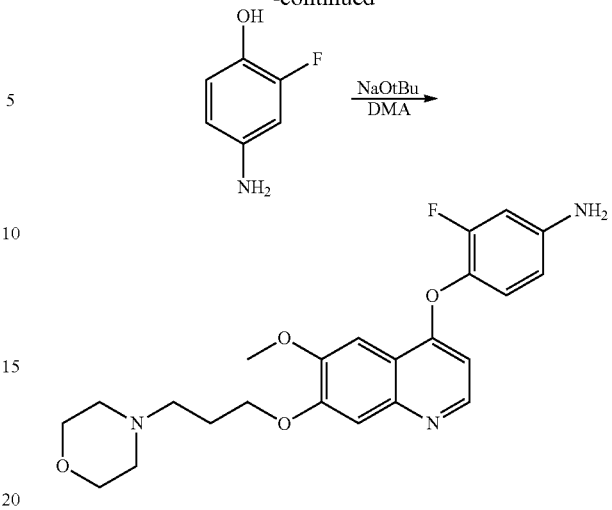

Solid sodium tert-butoxide (1.20 g; 12.5 mmol) was added to a suspension of the chloroquinoline (3.37 g; 10 mmol) in dimethylacetamide (35 mL), followed by solid 2-fluoro-4-hydroxyaniline. The dark green reaction mixture was heated at 95 to 100° C. for 18 hours. HPLC analysis showed approximately 18 percent starting material remaining and approximately 79 percent product. The reaction mixture was cooled to below 50° C., additional sodium tert-butoxide (300 mg; 3.125 mmol) and aniline (300 mg; 2.36 mmol) were added, and heating at 95 to 100° C. was resumed. HPLC analysis after 18 hours revealed less than 3 percent starting material remaining. The reaction was cooled to below 30° C., and ice water (50 mL) was added while maintaining the temperature below 30° C. After stirring for 1 hour at room temperature, the product was collected by filtration, washed with water (2×10 mL) and dried under vacuum on the filter funnel, to yield 4.11 g of the coupled product as a tan solid (96% yield; 89%, corrected for water content). $^1$H NMR and MS: consistent with product; 97.8% LCAP; approximately 7 weight percent water by KF.

Preparation of Compound 2 Hydrate Form

The hydrate of Compound 2 was prepared by adding 4.9614 g of Compound 1 and 50 mL of n-propanol to a 250 mL beaker. The suspension was heated to 90° C. with stirring via a magnetic stir bar at 200 rpm. After 2 hours, the solids were fully dissolved in an amber solution. At the 1 hour and 2 hour timepoints, 10 mL of n-propanol was added to account for evaporative effects and return the volume of the solution to 50 mL. The solution was then hot-filtered through a 1.6 μm glass fiber filter. The solution was then allowed to dry overnight in the beaker to a powder, which was then redissolved in 150 mL of a 1:1 mixture of acetone and water, and slurried overnight (16 hours) with a foil lid to prevent evaporation. The slurried solids were then collected by vacuum filtration. The final weight recovered was 3.7324 g (75% yield). This batch was stored at ambient conditions for several days prior to analysis.

Karl Fisher water content determinations were performed using a standard procedure. Water content was measured with a Brinkmann KF1V4 Metrohm 756 Coulometer equipped with a 703 Ti stirrer and using Hydranal Coulomat AG reagent. Samples were introduced into the vessel as solids. Approx 30-35 mg of sample was used per titration. A sample of crystalline Compound (I) prepared in Example 1.1.2 was measured in duplicate and was found to have an average water content be 2.5% w/w, with each replicate agreeing to within 0.1%.

A gravimetric vapor sorption (GVS) study was run using a standard procedure. Samples were run on a dynamic vapor sorption analyzer (Surface Measurement Systems) running DVSCFR software. Sample sizes were typically 10 mg. A moisture adsorption desorption isotherm was performed as outlined below. The standard isotherm experiment, performed at 25° C., is a two-cycle run, starting at 40% RH (relative humidity), increasing humidity to 90% RH, decreasing humidity to 0% RH, increasing humidity again to 90% RH, and finally decreasing humidity to 0% RH in 10% RH intervals. The crystalline Compound 1 prepared in Example 1.1.1 showed a 2.5% weight gain at 25° C. and 90% humidity. The GVS sorption and desorption curves showed evidence that the hydrate behaves as an isomorphic desolvate (Stephenson, G. A.; Groleau, E. G.; Kleeman, R. L.; Xu, W.; Rigsbee, D. R. *J. Pharm. Sci.* 1998, 87, 536-42).

The X-ray powder diffraction pattern of Compound 1 crystalline hydrate prepared above was acquired using a PANalytical X'Pert Pro diffractometer. The sample was gently flattened onto a zero-background silicon insert sample holder. A continuous 2θ scan range of 2° to 50° was used with a CuKα radiation source and a generator power of 40 kV and 45 mA. A 2θ step size of 0.017 degrees/step with a step time of 40.7 seconds was used. Samples were rotated at 30 rpm. Experiments were performed at room temperature and at ambient humidity. WO 2011/112896, the entire contents of which are incorporated herein by reference, shows the XRPD pattern for N-[3-fluoro-4-({6-(methyloxy)-7-[(3-morpholin-4-ylpropyl)oxy]quinolin-4-yl}oxy)phenyl]-N'-(4-fluorophenyl)cyclopropane-1,1-dicarboxamide crystalline hydrate. The following peaks at an experimental °2θ+0.1°2θ were identified in the XRPD pattern: 6.6, 9.0, 10.2, 12.0, 12.2, 13.1, 13.3, 14.6, 15.6, 16.2, 17.0, 17.1, 17.4, 18.2, 18.4, 18.7, 20.0, 20.3, 20.8, 21.7, 22.1, 23.1, 23.4, 23.8, 24.2, 24.5, 25.0. Only peaks below 25 °2θ are given as these are generally preferred for the identification of crystalline pharmaceutical forms. The entire list of peaks, or a subset thereof, may be sufficient to characterize the hydrate of Compound 1.

DSC thermograms were acquired using a TA Instruments Q2000 differential scanning calorimeter. A sample mass of 2.1500 mg of Compound 1 crystalline hydrate was weighed out directly into an aluminum DSC pan. The pan was sealed by applying pressure by hand and pushing each part the pan together (also known as a loose lid configuration). The temperature was ramped from 25° C. to 225° C. at 10° C./minute. A peak melting temperature of 137.4° C. and a heat flow of 44.2 J/g was measured for the melting endotherm. After the melting event, recrystallization occurs to an anhydrous form, which then melts at 194.1° C.

TGA thermograms were acquired using a TA Instruments Q500 Thermogravimetric Analyzer. The sample pan was tared, and 9.9760 milligrams of Compound (I) crystalline hydrate was placed in the pan. The temperature was ramped from 25° C. to 300° C. at 10° C./minute. A weight loss of 2.97% was observed up to 160° C., with an additional weight loss beyond 200° C. from decomposition.

Preparation of Compound 2 Crystalline Hydrate with Different Hydration States.

Five 150 mg aliquots were taken from the crystalline hydrate batch prepared above and were placed in 10 mL screw-top vials. With the vial tops removed, these aliquots were each stored in chambers with desiccant (Dri-Rite®, tricalcium silicate, RH 2-3%), saturated lithium bromide (6% RH), saturated lithium chloride (11% RH), saturated magnesium chloride (33% RH), and saturated sodium chloride (75% RH). The samples were removed after 2 weeks and immediately sealed with a cap for analysis and characterized.

The foregoing disclosure has been described in some detail by way of illustration and example, for purposes of clarity and understanding. The invention has been described with reference to various specific and preferred embodiments and techniques. However, it should be understood that many variations and modifications can be made while remaining within the spirit and scope of the invention. It will be obvious to one of skill in the art that changes and modifications can be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

What is claimed is:

1. A process for preparing a compound of Formula A:

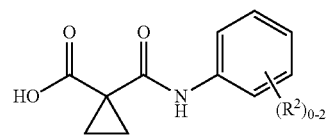

wherein $R^2$ is H, F, Cl, or Br;
comprising
(a) contacting 1,1-cyclopropane dicarboxylic acid with thionyl chloride in a polar aprotic solvent at room temperature; and
(b) adding

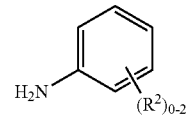

and a tertiary amine base to the mixture of step (a).

2. The process of claim 1, wherein the polar aprotic solvent is selected from the group consisting of dichloromethane, tetrahydrofuran, ethyl acetate, isopropyl acetate, acetone, dimethylformamide, acetonitrile, and dimethylsulfoxide, or combinations thereof.

3. The process of claim 1, wherein the polar aprotic solvent is isopropyl acetate.

4. The process of claim 1, wherein approximately 5 to 10 volumes of polar aprotic solvent are used relative to the volume of 1,1-cyclopropanedicarboxylic acid that is used.

5. The process of claim 1, wherein approximately 8 volumes of polar aprotic solvent are used relative to the volume of 1,1-cyclopropanedicarboxylic acid that is used.

6. The process of claim 1, wherein approximately 1.01 to 1.2 molar equivalents of thionyl chloride are used.

7. The process of claim 1, wherein approximately 1.05 molar equivalents of thionyl chloride are used.

8. The process of claim 1, wherein the mixture of step (a) is stirred at ambient temperature for 2 to 24 hours.

9. The process of claim 1, wherein the mixture of step (a) is stirred at approximately 24-26° C. for 6 to 16 hours.

10. The process for claim 1, wherein the optionally substituted aniline and the tertiary amine base in step (b) are added as a mixture in a polar aprotic solvent to the step (a) mixture.

11. The process for claim 10, wherein the aniline is 4-fluoroaniline and the tertiary amine base is triethyl amine.

12. The process of claim 10, wherein approximately 1.01 to 1.5 molar equivalents of are used relative to the number of moles of 1,1-cyclopropanedicarboxylic acid that are used and approximately 1.01 to 1.5 molar equivalents of tertiary amine base are used relative to the number of moles of 1,1-cyclopropanedicarboxylic acid that are used.

13. The process of claim 10, wherein the polar aprotic solvent in step (b) is selected from the group consisting of dichloromethane, tetrahydrofuran, ethyl acetate, isopropyl acetate, acetone, dimethylformamide, acetonitrile, and dimethylsulfoxide, or combinations thereof.

14. The process of claim 10, wherein the polar aprotic solvent in step (b) is isopropyl acetate.

15. The process of claim 14, wherein approximately 2 volumes of isopropyl acetate are used.

16. The process of claim 1, wherein the resulting mixture of step (b) is allowed to stir for approximately 0.75 to 4 hours at ambient temperature.

17. The process of claim 1, further comprising quenching the resulting mixture of step (b) with a concentrated aqueous base.

18. The process for claim 17, wherein the aqueous base is selected from the group consisting of NaOH, KOH, or $K_3PO_4$.

19. A process for preparing a compound of Formula A

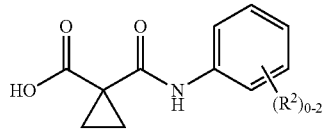

wherein $R^2$ is H, F, Cl, or Br;
comprising
(a) contacting 1,1-cyclopropane dicarboxylic acid with thionyl chloride in isopropyl acetate at room temperature;
(b) adding

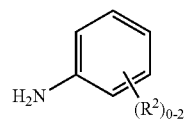

and triethyl amine to the mixture of step (a);
(c) quenching the resulting mixture in step (b) with concentrated aqueous sodium hydroxide;
(d) extracting the compound of Formula A into dilute aqueous base;
(e) acidifying the mixture with HCl; and
(f) isolating the compound of Formula A by filtration.

20. A process for preparing a compound of Formula A-1:

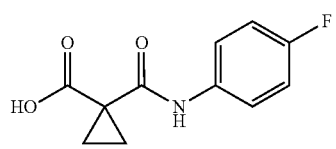

comprising
(a) contacting 1,1-cyclopropane dicarboxylic acid with thionyl chloride in isopropyl acetate at room temperature; and
(b) adding a mixture comprising 4-fluoroaniline and a triethyl amine in isopropyl acetate to the mixture of step (a).

21. A process for preparing a compound of Formula A-1:

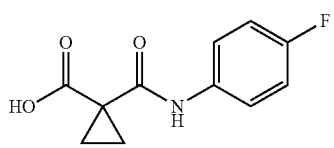

comprising
(a) contacting 1,1-cyclopropane dicarboxylic acid with thionyl chloride in isopropyl acetate at room temperature;
(b) adding a mixture comprising 4-fluoroaniline and a triethyl amine in isopropyl acetate to the mixture of step (a);
(c) quenching the resulting mixture of step (b) with concentrated aqueous sodium hydroxide;
(d) extracting the compound of Formula A-1 into dilute aqueous base;
(e) acidifying the mixture of step (d) with HCl; and
(f) isolating the compound of Formula A-1 by filtration.

22. The process of claim 1, wherein the compound of Formula A is contaminated with approximately 5 percent or less of the bisamide

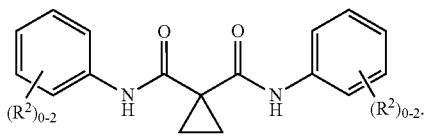

23. A process for preparing a compound of Formula I:

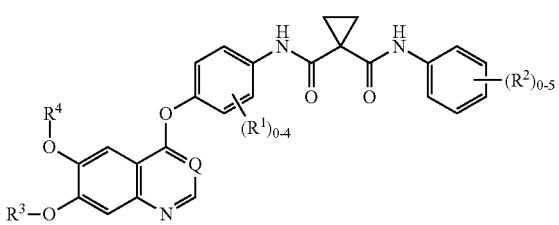

wherein:
$R^1$ is halo;
$R^2$ is halo;
$R^3$ is $(C_1-C_6)$alkyl or $(C_1-C_6)$alkyl optionally substituted with heterocycloalkyl;
$R^4$ is $(C_1-C_6)$alkyl; and
Q is CH or N;

comprising:
(a) contacting 1,1-cyclopropane dicarboxylic acid with thionyl chloride in a polar aprotic solvent;
(b) adding

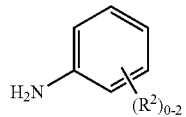

and a tertiary amine base to the mixture of step (a) to form a compound of Formula A

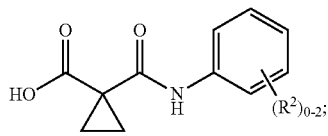

(c) coupling a compound of Formula A with an amine of Formula B to form a compound of Formula I

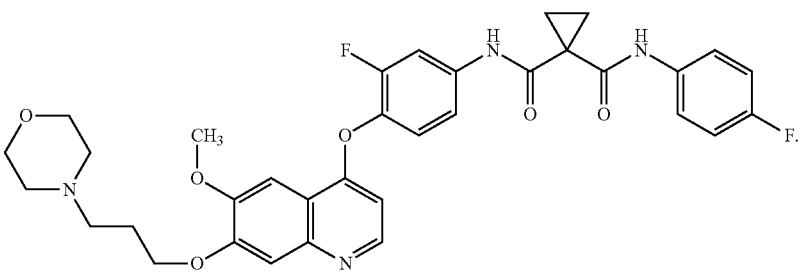

24. The process of claim 23, wherein the compound of Formula I is compound 1

Compound 1

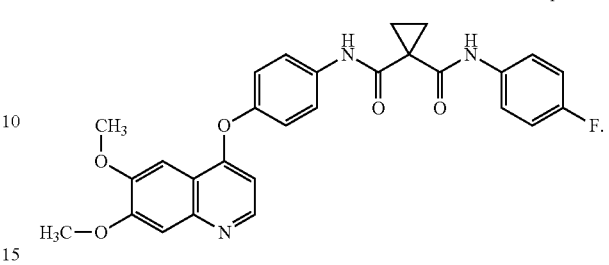

25. The process of claim 23, wherein the compound of Formula I is compound 2

Compound 2

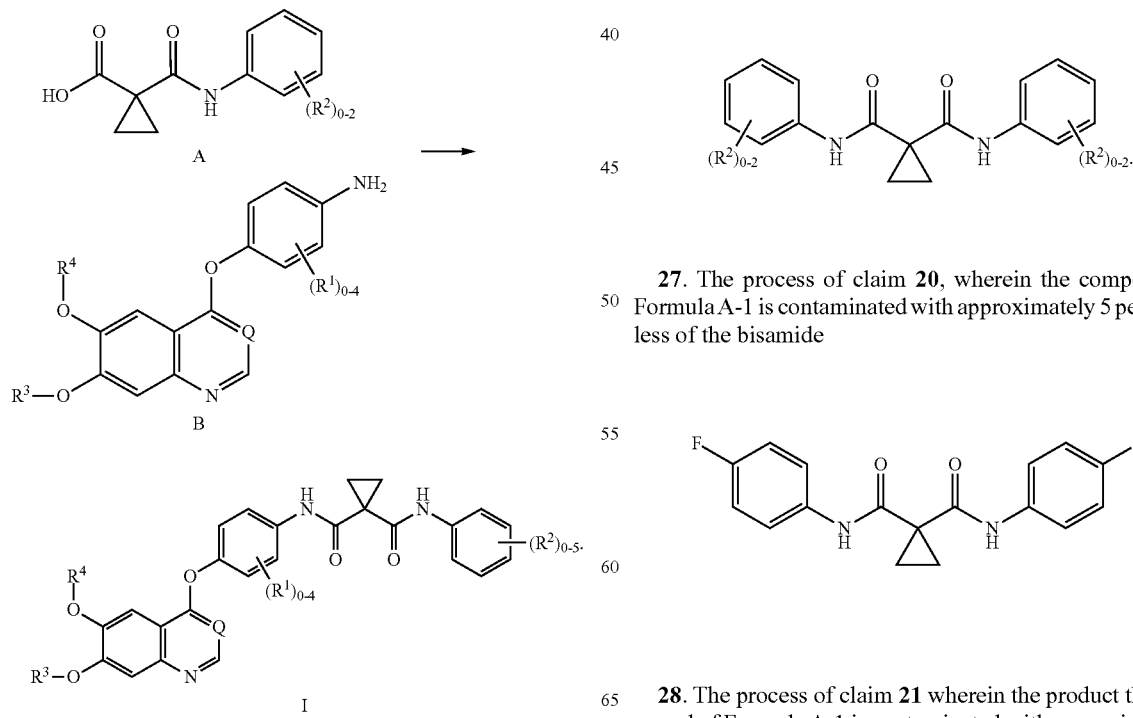

26. The process of claim 19, wherein the compound of Formula A is contaminated with approximately 5 percent or less of the bisamide

27. The process of claim 20, wherein the compound of Formula A-1 is contaminated with approximately 5 percent or less of the bisamide

28. The process of claim 21 wherein the product the compound of Formula A-1 is contaminated with approximately 5 percent or less of the bisamide

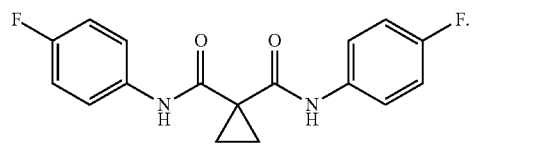 [SMILES: O=C(Nc1ccc(F)cc1)C1(C(=O)Nc2ccc(F)cc2)CC1]
* * * * *